(12) United States Patent
Teichman et al.

(10) Patent No.: US 7,987,001 B2
(45) Date of Patent: Jul. 26, 2011

(54) SURGICAL NAVIGATIONAL AND NEUROMONITORING INSTRUMENT

(75) Inventors: Robert Teichman, Lafayette, CO (US); Laurent Verard, Superior, CO (US); Eric Ryterski, Louisville, CO (US); W. Keith Adcox, Memphis, TN (US); John B. Clayton, Superior, CO (US); David Mire, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1038 days.

(21) Appl. No.: 11/626,917

(22) Filed: Jan. 25, 2007

(65) Prior Publication Data

US 2008/0183189 A1 Jul. 31, 2008

(51) Int. Cl.
*A61N 1/18* (2006.01)

(52) U.S. Cl. .......................... 607/151; 606/32

(58) Field of Classification Search .................. 607/145, 607/150, 151
See application file for complete search history.

(56) References Cited

U.S. PATENT DOCUMENTS

| | | |
|---|---|---|
| 2,429,968 A | 10/1947 | Stanphill |
| 2,669,986 A | 2/1954 | Crawley |
| 2,704,064 A | 3/1955 | Fizzell et al. |
| 3,313,293 A | 4/1967 | Chesebrough et al. |
| 3,336,916 A | 8/1967 | Edlich |
| 3,598,108 A | 8/1971 | Jamshidi et al. |
| 3,628,524 A | 12/1971 | Jamshidi |
| 3,630,192 A | 12/1971 | Jamshidi |
| 3,664,329 A | 5/1972 | Naylor |
| 3,682,162 A | 8/1972 | Colyer |
| 3,785,368 A | 1/1974 | McCarthy et al. |
| 3,800,783 A | 4/1974 | Jamshidi |
| 3,830,226 A | 8/1974 | Staub et al. |
| 3,929,123 A | 12/1975 | Jamshidi |
| 4,163,446 A | 8/1979 | Jamshidi |
| 4,235,242 A | 11/1980 | Howson et al. |
| 4,248,240 A | 2/1981 | van Eykern |
| 4,262,676 A | 4/1981 | Jamshidi |
| 4,266,555 A | 5/1981 | Jamshidi |
| 4,344,440 A | 8/1982 | Aaby et al. |
| 4,356,828 A | 11/1982 | Jamshidi |
| 4,493,327 A | 1/1985 | Bergelson et al. |
| 4,515,168 A | 5/1985 | Chester et al. |
| 4,824,433 A | 4/1989 | Marz et al. |
| 4,892,105 A | 1/1990 | Prass |
| 4,920,979 A | 5/1990 | Bullara |
| 4,934,377 A | 6/1990 | Bova et al. |

(Continued)

FOREIGN PATENT DOCUMENTS

GB 2356051 9/2001

(Continued)

OTHER PUBLICATIONS

Unpublished U.S. Appl. No. 11/626,901, filed Jan. 25, 2007 titled "Integrated Surgical Navigational and Neuromonitoring System".

(Continued)

*Primary Examiner* — Carl H Layno
*Assistant Examiner* — Brian T Gedeon

(57) ABSTRACT

The invention relates to a surgical instrument capable of applying an electrostimulation to a neural structure. The surgical instrument also has a tracking system associated therewith to provide navigational tracking during a surgical procedure.

17 Claims, 11 Drawing Sheets

U.S. PATENT DOCUMENTS

| | | | |
|---|---|---|---|
| 4,955,810 A | 9/1990 | Levy | |
| 4,962,766 A | 10/1990 | Herzon | |
| 5,007,902 A | 4/1991 | Witt | |
| 5,024,228 A | 6/1991 | Goldstone et al. | |
| 5,046,506 A | 9/1991 | Singer | |
| 5,078,147 A | 1/1992 | Reid | |
| 5,080,104 A | 1/1992 | Marks et al. | |
| 5,081,990 A | 1/1992 | Deletis | |
| 5,125,406 A | 6/1992 | Goldstone et al. | |
| 5,161,533 A | 11/1992 | Prass et al. | |
| 5,196,015 A | 3/1993 | Neubardt | |
| 5,201,903 A | 4/1993 | Corbett, III et al. | |
| 5,203,330 A | 4/1993 | Schaefer et al. | |
| 5,215,095 A | 6/1993 | Macvicar | |
| 5,255,677 A | 10/1993 | Schaefer et al. | |
| 5,271,413 A | 12/1993 | Dalamagas et al. | |
| 5,284,153 A | 2/1994 | Raymond et al. | |
| 5,284,154 A | 2/1994 | Raymond et al. | |
| 5,313,956 A | 5/1994 | Knutsson et al. | |
| 5,320,101 A | 6/1994 | Faupel et al. | |
| 5,335,668 A | 8/1994 | Nardella | |
| 5,383,454 A | 1/1995 | Bucholz | |
| 5,388,587 A | 2/1995 | Knutsson et al. | |
| 5,421,727 A | 6/1995 | Stevens et al. | |
| 5,462,065 A | 10/1995 | Cusimano | |
| 5,474,558 A | 12/1995 | Neubardt | |
| 5,513,651 A | 5/1996 | Cusimano et al. | |
| 5,515,848 A | 5/1996 | Corbett, III et al. | |
| 5,524,632 A | 6/1996 | Stein et al. | |
| 5,526,821 A | 6/1996 | Jamshidi | |
| 5,532,613 A | 7/1996 | Nagasawa et al. | |
| 5,540,235 A | 7/1996 | Wilson | |
| 5,560,372 A | 10/1996 | Cory | |
| 5,564,078 A | 10/1996 | Nagai | |
| 5,564,079 A | 10/1996 | Olsson | |
| 5,630,422 A | 5/1997 | Zanakis | |
| 5,630,839 A | 5/1997 | Corbett, III et al. | |
| D387,427 S | 12/1997 | Bucholz et al. | |
| 5,692,516 A | 12/1997 | Kaneko et al. | |
| 5,775,331 A | 7/1998 | Raymond et al. | |
| 5,779,642 A | 7/1998 | Nightengale | |
| 5,792,212 A | 8/1998 | Weijand | |
| 5,800,500 A | 9/1998 | Spelman et al. | |
| 5,807,275 A | 9/1998 | Jamshidi | |
| 5,830,151 A | 11/1998 | Hadzic et al. | |
| 5,843,148 A | 12/1998 | Gijsbers et al. | |
| 5,851,183 A | 12/1998 | Bucholz | |
| 5,851,191 A | 12/1998 | Gozani | |
| 5,853,373 A | 12/1998 | Griffith et al. | |
| 5,860,939 A | 1/1999 | Wofford et al. | |
| 5,871,445 A | 2/1999 | Bucholz | |
| 5,885,219 A | 3/1999 | Nightengale | |
| 5,891,034 A | 4/1999 | Bucholz | |
| 5,928,158 A | 7/1999 | Aristides | |
| 5,941,876 A | 8/1999 | Nardella et al. | |
| 5,947,972 A | 9/1999 | Gage et al. | |
| 5,970,499 A | 10/1999 | Smith et al. | |
| 5,976,094 A | 11/1999 | Gozani | |
| 5,987,960 A | 11/1999 | Messner et al. | |
| 6,002,957 A | 12/1999 | Finneran | |
| 6,002,964 A | 12/1999 | Feler et al. | |
| 6,004,312 A | 12/1999 | Finneran et al. | |
| 6,011,996 A | 1/2000 | Gielen et al. | |
| D420,132 S | 2/2000 | Bucholz et al. | |
| 6,021,343 A * | 2/2000 | Foley et al. | 600/429 |
| 6,027,456 A | 2/2000 | Feler et al. | |
| D422,706 S | 4/2000 | Bucholz et al. | |
| 6,076,008 A | 6/2000 | Bucholz | |
| 6,104,957 A | 8/2000 | Alo et al. | |
| 6,118,845 A | 9/2000 | Simon et al. | |
| 6,132,386 A | 10/2000 | Gozani et al. | |
| 6,167,145 A | 12/2000 | Foley et al. | |
| 6,173,300 B1 | 1/2001 | Mahurin | |
| 6,181,961 B1 | 1/2001 | Prass | |
| 6,187,018 B1 | 2/2001 | Sanjay-Gopal et al. | |
| 6,190,395 B1 | 2/2001 | Williams | |
| 6,193,715 B1 | 2/2001 | Wrublewski et al. | |
| 6,224,549 B1 | 5/2001 | Drongelen | |
| 6,224,603 B1 | 5/2001 | Marino | |
| 6,226,548 B1 | 5/2001 | Foley et al. | |
| 6,235,038 B1 | 5/2001 | Hunter et al. | |
| 6,236,875 B1 | 5/2001 | Bucholz et al. | |
| 6,253,210 B1 | 6/2001 | Smith et al. | |
| 6,259,945 B1 | 7/2001 | Epstein et al. | |
| 6,266,558 B1 | 7/2001 | Gozani et al. | |
| 6,292,701 B1 | 9/2001 | Prass et al. | |
| 6,298,256 B1 | 10/2001 | Meyer | |
| 6,298,262 B1 | 10/2001 | Franck et al. | |
| 6,304,776 B1 | 10/2001 | Muntermann | |
| 6,306,100 B1 | 10/2001 | Prass | |
| 6,306,403 B1 | 10/2001 | Donovan | |
| 6,312,392 B1 | 11/2001 | Herzon | |
| 6,314,315 B1 | 11/2001 | Hung et al. | |
| 6,325,762 B1 | 12/2001 | Tjin | |
| 6,330,466 B1 | 12/2001 | Hofmann et al. | |
| 6,334,068 B1 | 12/2001 | Hacker | |
| 6,337,994 B1 | 1/2002 | Stoianovici et al. | |
| 6,340,363 B1 | 1/2002 | Bolger et al. | |
| 6,347,240 B1 | 2/2002 | Foley et al. | |
| 6,348,058 B1 | 2/2002 | Melkent et al. | |
| 6,351,659 B1 | 2/2002 | Vilsmeier | |
| 6,374,135 B1 | 4/2002 | Bucholz | |
| 6,379,302 B1 | 4/2002 | Kessman et al. | |
| 6,379,313 B1 | 4/2002 | Gozani et al. | |
| 6,381,485 B1 | 4/2002 | Hunter et al. | |
| 6,391,005 B1 | 5/2002 | Lum et al. | |
| 6,402,762 B2 | 6/2002 | Hunter et al. | |
| 6,434,415 B1 | 8/2002 | Foley et al. | |
| 6,434,507 B1 | 8/2002 | Clayton et al. | |
| 6,456,874 B1 | 9/2002 | Hafer et al. | |
| 6,463,319 B1 | 10/2002 | Bucholz | |
| 6,466,817 B1 | 10/2002 | Kaula et al. | |
| 6,470,207 B1 | 10/2002 | Simon et al. | |
| 6,474,341 B1 | 11/2002 | Hunter et al. | |
| 6,490,467 B1 | 12/2002 | Bucholz et al. | |
| 6,491,699 B1 | 12/2002 | Henderson et al. | |
| 6,500,128 B2 | 12/2002 | Marino | |
| 6,526,415 B2 | 2/2003 | Smith et al. | |
| 6,533,732 B1 | 3/2003 | Urmey | |
| 6,535,756 B1 | 3/2003 | Simon et al. | |
| 6,535,759 B1 | 3/2003 | Epstein et al. | |
| 6,540,668 B1 | 4/2003 | Schulz et al. | |
| 6,553,152 B1 | 4/2003 | Miller et al. | |
| 6,560,479 B2 | 5/2003 | van Drongelen | |
| 6,564,078 B1 | 5/2003 | Marino et al. | |
| 6,579,244 B2 | 6/2003 | Goodwin | |
| 6,636,757 B1 | 10/2003 | Jascob et al. | |
| 6,654,634 B1 | 11/2003 | Prass | |
| 6,669,242 B2 | 12/2003 | Fountaine et al. | |
| 6,669,635 B2 | 12/2003 | Kessman et al. | |
| 6,671,550 B2 | 12/2003 | Iaizzo et al. | |
| 6,674,916 B1 | 1/2004 | Deman et al. | |
| 6,678,545 B2 | 1/2004 | Bucholz | |
| 6,678,550 B2 | 1/2004 | Hubbard, Jr. | |
| 6,694,162 B2 | 2/2004 | Hartlep | |
| 6,708,184 B2 | 3/2004 | Smith et al. | |
| 6,725,078 B2 | 4/2004 | Bucholz et al. | |
| 6,725,080 B2 | 4/2004 | Melkent et al. | |
| 6,725,086 B2 | 4/2004 | Marinello | |
| 6,735,711 B2 | 5/2004 | Lutz | |
| 6,748,276 B1 | 6/2004 | Daignault, Jr. et al. | |
| 6,754,374 B1 | 6/2004 | Miller et al. | |
| 6,760,616 B2 | 7/2004 | Hoey et al. | |
| 6,796,985 B2 | 9/2004 | Bolger et al. | |
| 6,796,988 B2 | 9/2004 | Estes et al. | |
| 6,807,444 B2 | 10/2004 | Tu et al. | |
| 6,832,111 B2 | 12/2004 | Tu et al. | |
| 6,849,047 B2 | 2/2005 | Goodwin | |
| 6,859,660 B2 | 2/2005 | Vilsmeier | |
| 6,862,469 B2 | 3/2005 | Bucholz et al. | |
| 6,892,090 B2 | 5/2005 | Verard et al. | |
| 6,896,675 B2 | 5/2005 | Leung et al. | |
| 6,920,347 B2 | 7/2005 | Simon et al. | |
| 6,928,490 B1 | 8/2005 | Bucholz et al. | |
| 6,960,208 B2 | 11/2005 | Bourne et al. | |
| 6,978,166 B2 | 12/2005 | Foley et al. | |
| 7,001,045 B2 | 2/2006 | Gregerson et al. | |

| | | |
|---|---|---|
| 7,007,699 B2 | 3/2006 | Martinelli et al. |
| 7,050,848 B2 | 5/2006 | Hoey et al. |
| 7,052,494 B2 | 5/2006 | Goble et al. |
| RE39,133 E | 6/2006 | Clayton et al. |
| 7,072,704 B2 | 7/2006 | Bucholz |
| 7,079,883 B2 | 7/2006 | Marino et al. |
| 2001/0027271 A1 | 10/2001 | Franck et al. |
| 2001/0029509 A1 | 10/2001 | Smith et al. |
| 2001/0049475 A1 | 12/2001 | Bucholz et al. |
| 2002/0007129 A1 | 1/2002 | Marino |
| 2002/0035321 A1 | 3/2002 | Bucholz et al. |
| 2002/0052610 A1 | 5/2002 | Skakoon et al. |
| 2002/0072686 A1 | 6/2002 | Hoey et al. |
| 2002/0087075 A1 | 7/2002 | Bucholz |
| 2002/0095081 A1 | 7/2002 | Vilsmeier |
| 2002/0156372 A1 | 10/2002 | Skakoon et al. |
| 2002/0161372 A1 | 10/2002 | Bolger et al. |
| 2002/0183610 A1 | 12/2002 | Foley et al. |
| 2002/0183615 A1 | 12/2002 | Bucholz |
| 2002/0183647 A1 | 12/2002 | Gozani et al. |
| 2003/0018247 A1 | 1/2003 | Gonzalez |
| 2003/0045808 A1 | 3/2003 | Kaula et al. |
| 2003/0069514 A1 | 4/2003 | Brody |
| 2003/0088185 A1 | 5/2003 | Prass |
| 2003/0093007 A1 | 5/2003 | Wood |
| 2003/0105503 A1 | 6/2003 | Marino |
| 2003/0114752 A1 | 6/2003 | Henderson et al. |
| 2003/0133187 A1 | 7/2003 | Schmidt et al. |
| 2003/0139781 A1 | 7/2003 | Bradley et al. |
| 2003/0163060 A1 | 8/2003 | Maddess et al. |
| 2003/0167021 A1 | 9/2003 | Shimm |
| 2003/0195405 A1 | 10/2003 | Marino et al. |
| 2003/0202990 A1 | 10/2003 | Donovan et al. |
| 2003/0209096 A1 | 11/2003 | Pandey et al. |
| 2004/0010204 A1 | 1/2004 | Weber et al. |
| 2004/0049231 A1 | 3/2004 | Hafer |
| 2004/0054273 A1 | 3/2004 | Finneran et al. |
| 2004/0054274 A1 | 3/2004 | Finneran et al. |
| 2004/0054275 A1 | 3/2004 | Finneran et al. |
| 2004/0054276 A1 | 3/2004 | Finneran et al. |
| 2004/0059247 A1 | 3/2004 | Urmey |
| 2004/0106916 A1 | 6/2004 | Quaid et al. |
| 2004/0111118 A1 | 6/2004 | Hill et al. |
| 2004/0122482 A1 | 6/2004 | Tung et al. |
| 2004/0176759 A1 | 9/2004 | Krishnamurthy et al. |
| 2004/0186531 A1 | 9/2004 | Jahns et al. |
| 2004/0186532 A1 | 9/2004 | Tadlock |
| 2004/0199068 A1 | 10/2004 | Bucholz et al. |
| 2004/0199084 A1 | 10/2004 | Kelleher et al. |
| 2004/0225228 A1 | 11/2004 | Ferree |
| 2004/0243206 A1 | 12/2004 | Tadlock |
| 2004/0243207 A1 | 12/2004 | Olson et al. |
| 2004/0243208 A1 | 12/2004 | Jordan |
| 2004/0249373 A1 | 12/2004 | Gronemeyer et al. |
| 2004/0249429 A1 | 12/2004 | Tadlock |
| 2004/0260357 A1 | 12/2004 | Vaughan et al. |
| 2004/0260358 A1 | 12/2004 | Vaughan et al. |
| 2005/0004623 A1 | 1/2005 | Miles et al. |
| 2005/0010262 A1 | 1/2005 | Rezai et al. |
| 2005/0027284 A1 | 2/2005 | Lozano et al. |
| 2005/0033379 A1 | 2/2005 | Lozano et al. |
| 2005/0033393 A1 | 2/2005 | Daglow |
| 2005/0075578 A1 | 4/2005 | Gharib et al. |
| 2005/0085743 A1 | 4/2005 | Hacker et al. |
| 2005/0113882 A1 | 5/2005 | Cameron et al. |
| 2005/0119660 A1* | 6/2005 | Bourlion et al. ............... 606/80 |
| 2005/0149035 A1 | 7/2005 | Pimenta et al. |
| 2005/0159797 A1 | 7/2005 | Chandran et al. |
| 2005/0171558 A1* | 8/2005 | Abovitz et al. ............... 606/130 |
| 2005/0171576 A1 | 8/2005 | Williams et al. |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0182454 A1 | 8/2005 | Gharib et al. |
| 2005/0261602 A1 | 11/2005 | Mumford et al. |
| 2005/0277918 A1 | 12/2005 | Shah et al. |
| 2005/0283148 A1 | 12/2005 | Janssen |
| 2006/0025702 A1 | 2/2006 | Sterrantino et al. |
| 2006/0025703 A1 | 2/2006 | Miles et al. |
| 2006/0085049 A1 | 4/2006 | Cory |
| 2006/0085409 A1 | 4/2006 | Rys et al. |
| 2006/0089633 A1 | 4/2006 | Bleich et al. |
| 2006/0089640 A1 | 4/2006 | Bleich et al. |
| 2006/0094976 A1 | 5/2006 | Bleich |
| 2006/0095028 A1 | 5/2006 | Bleich |
| 2006/0100651 A1 | 5/2006 | Bleich |
| 2006/0111767 A1 | 5/2006 | Olson et al. |
| 2006/0122458 A1 | 6/2006 | Bleich |
| 2006/0122483 A1 | 6/2006 | Foley et al. |
| 2006/0135882 A1 | 6/2006 | Bleich |
| 2006/0161058 A1 | 7/2006 | Ives et al. |
| 2006/0173374 A1 | 8/2006 | Neubardt et al. |
| 2006/0173521 A1 | 8/2006 | Pond, Jr. et al. |
| 2006/0178593 A1 | 8/2006 | Neubardt et al. |
| 2006/0178594 A1 | 8/2006 | Neubardt et al. |
| 2006/0200207 A1 | 9/2006 | Thrope et al. |
| 2006/0200219 A1 | 9/2006 | Thrope et al. |
| 2006/0217610 A1 | 9/2006 | Prass |
| 2006/0217655 A1 | 9/2006 | Vitullo et al. |
| 2006/0224078 A1 | 10/2006 | Hoey et al. |
| 2006/0224219 A1 | 10/2006 | Podhajsky et al. |
| 2006/0241628 A1 | 10/2006 | Parak |

FOREIGN PATENT DOCUMENTS

| | | |
|---|---|---|
| JP | 5-49644 | 2/1993 |
| WO | WO 94/24933 | 11/1994 |
| WO | WO 96/11624 | 4/1996 |
| WO | WO 97/13454 | 4/1997 |
| WO | WO 97/26836 | 7/1997 |
| WO | WO 00/19892 | 4/2000 |
| WO | WO 01/37728 | 5/2001 |
| WO | WO 01/76498 | 10/2001 |
| WO | WO 01/93759 | 12/2001 |
| WO | WO 03/005887 | 1/2003 |
| WO | WO 03/026482 | 4/2003 |
| WO | WO 03/037170 | 5/2003 |
| WO | WO 03/105709 | 12/2003 |
| WO | WO 2004/064634 | 8/2004 |
| WO | WO 2005/074831 | 8/2005 |

OTHER PUBLICATIONS

Unpublished U.S. Appl. No. 11/626,910, filed Jan. 25, 2007 titled "Integrated Visualization of Surgical Navigational and Neural Monitoring Information".

Unpublished U.S. Appl. No. 11/626,942, filed Jan. 25, 2007 titled "Integrated Surgical Navigational and Neuromonitoring System Having Automated Surgical Assistance and Control".

Unpublished U.S. Appl. No. 11/626,954, filed Jan. 25, 2007 titled Method and Apparatus for Coordinated Display of Anatomical and Neuromonitoring Information.

"Universal Orthopaedic Navigation Image-Guided Universal Hip Replacement Surgery", Medtronic Surgical Navigation Technologies, 2003.

"StealthStation AxiEM Electromagnetic Navigation Technology", Medtronic Navigation, Inc., 2005.

"SonoNav", Medtronic Navigation, Inc., 2005.

* cited by examiner

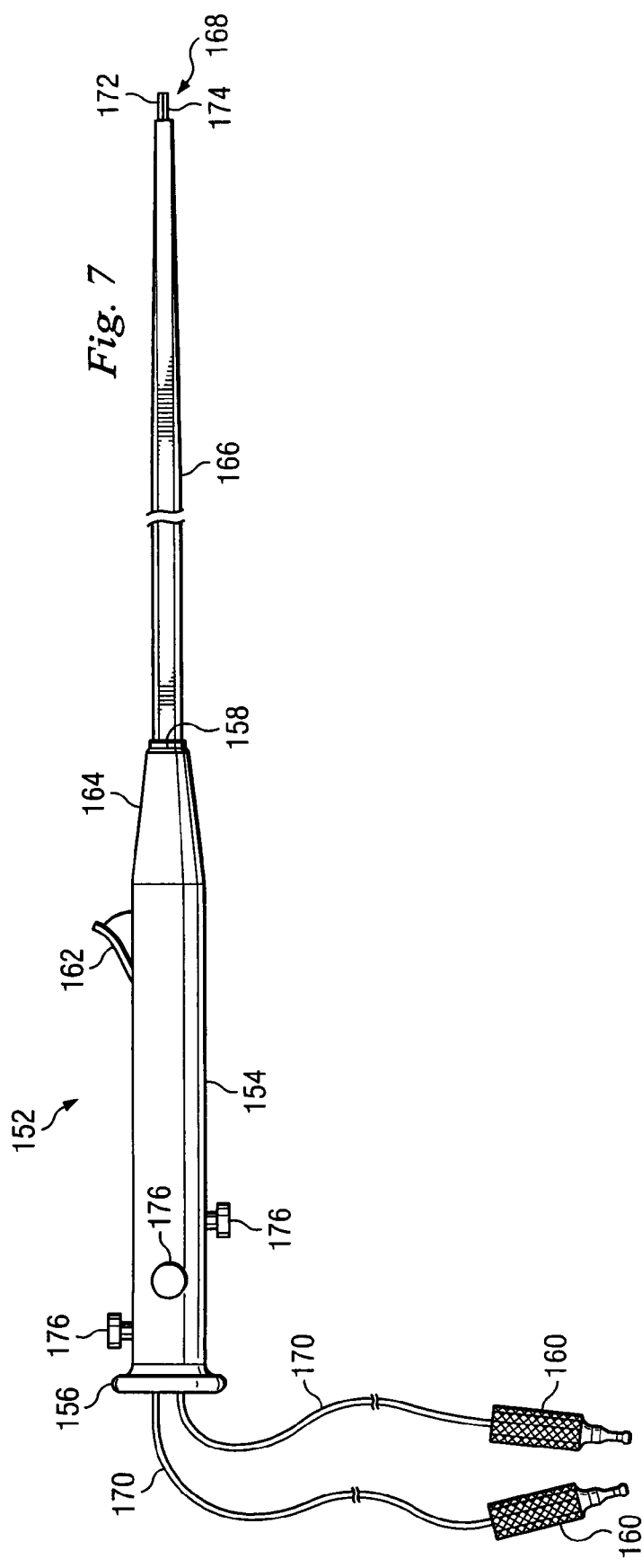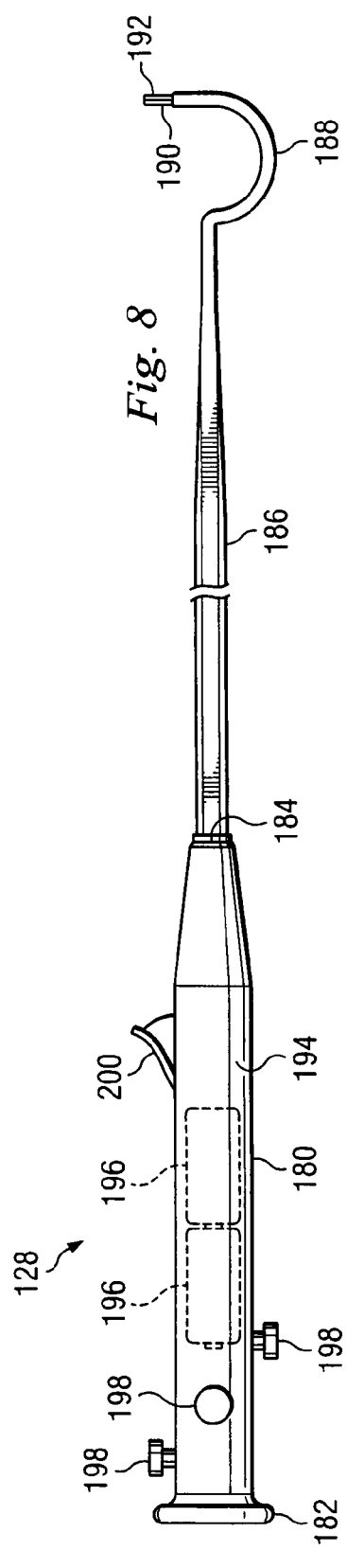

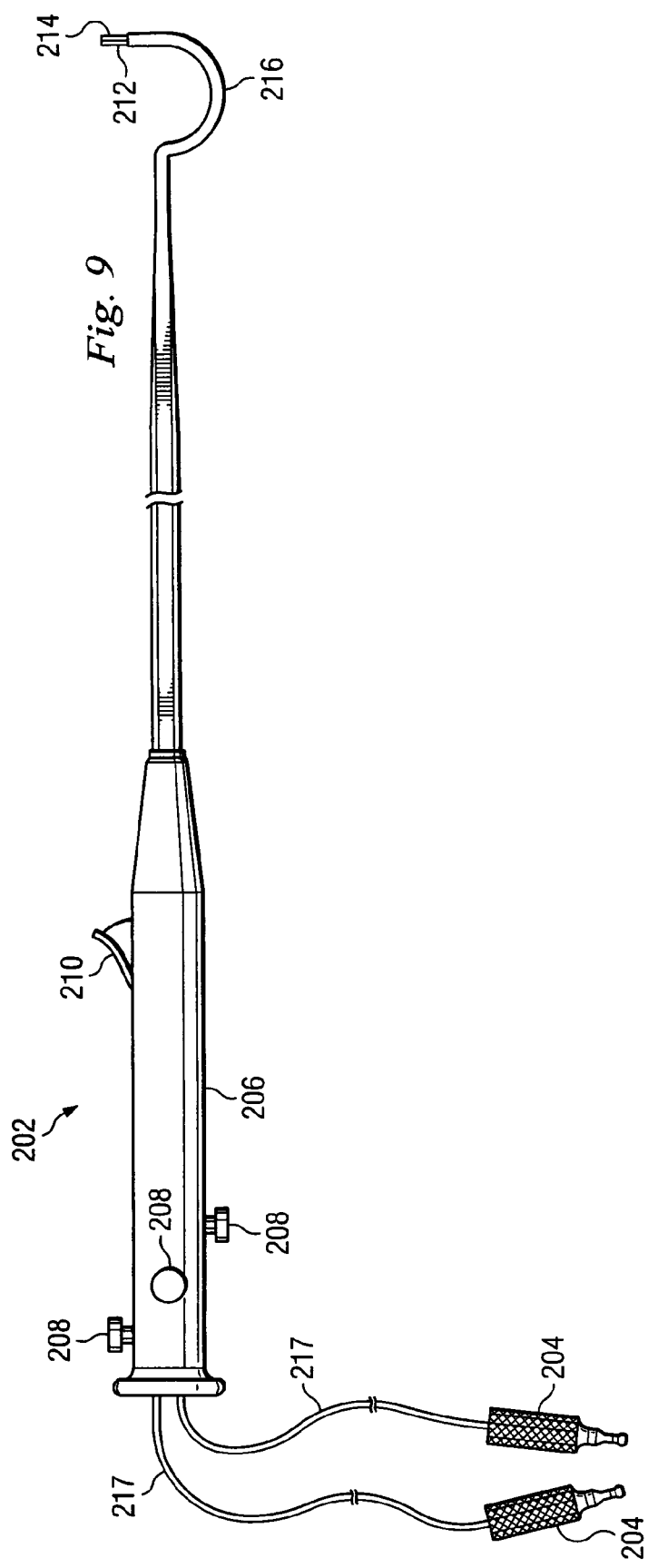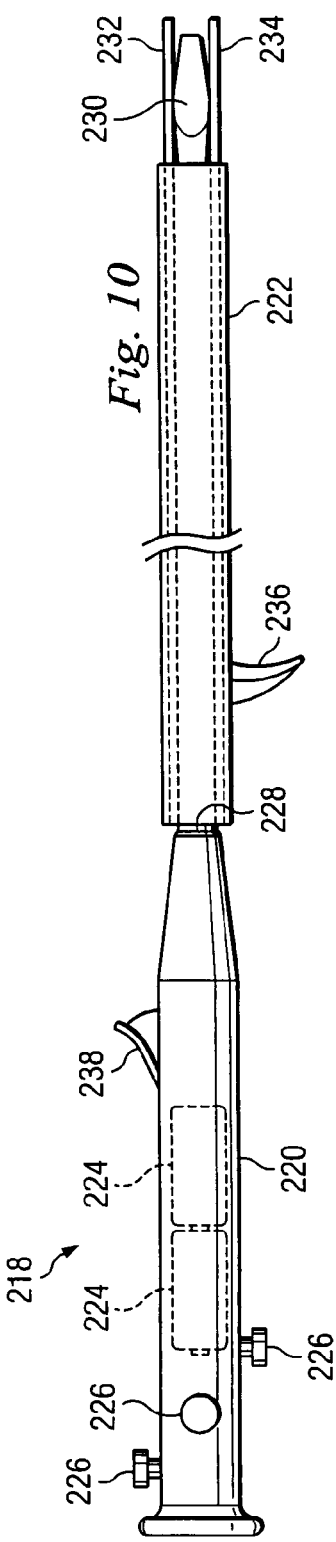

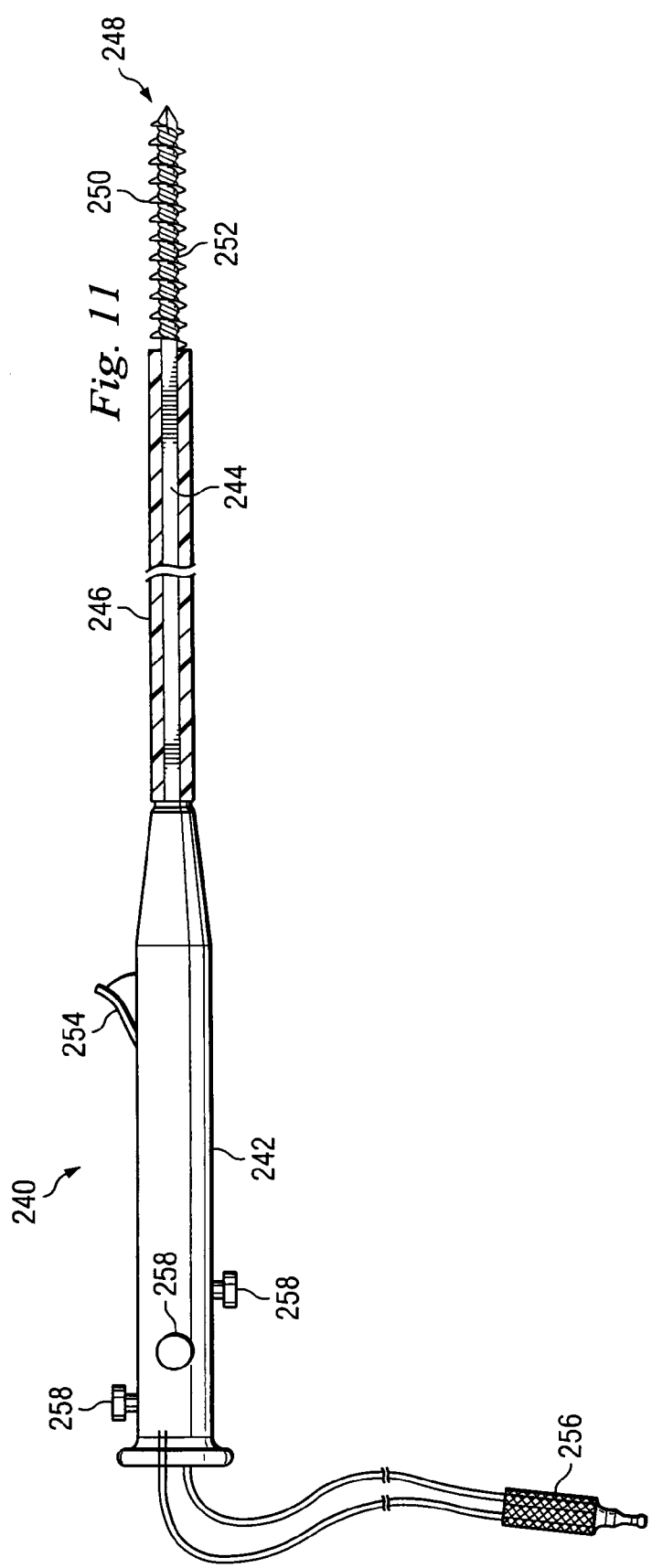

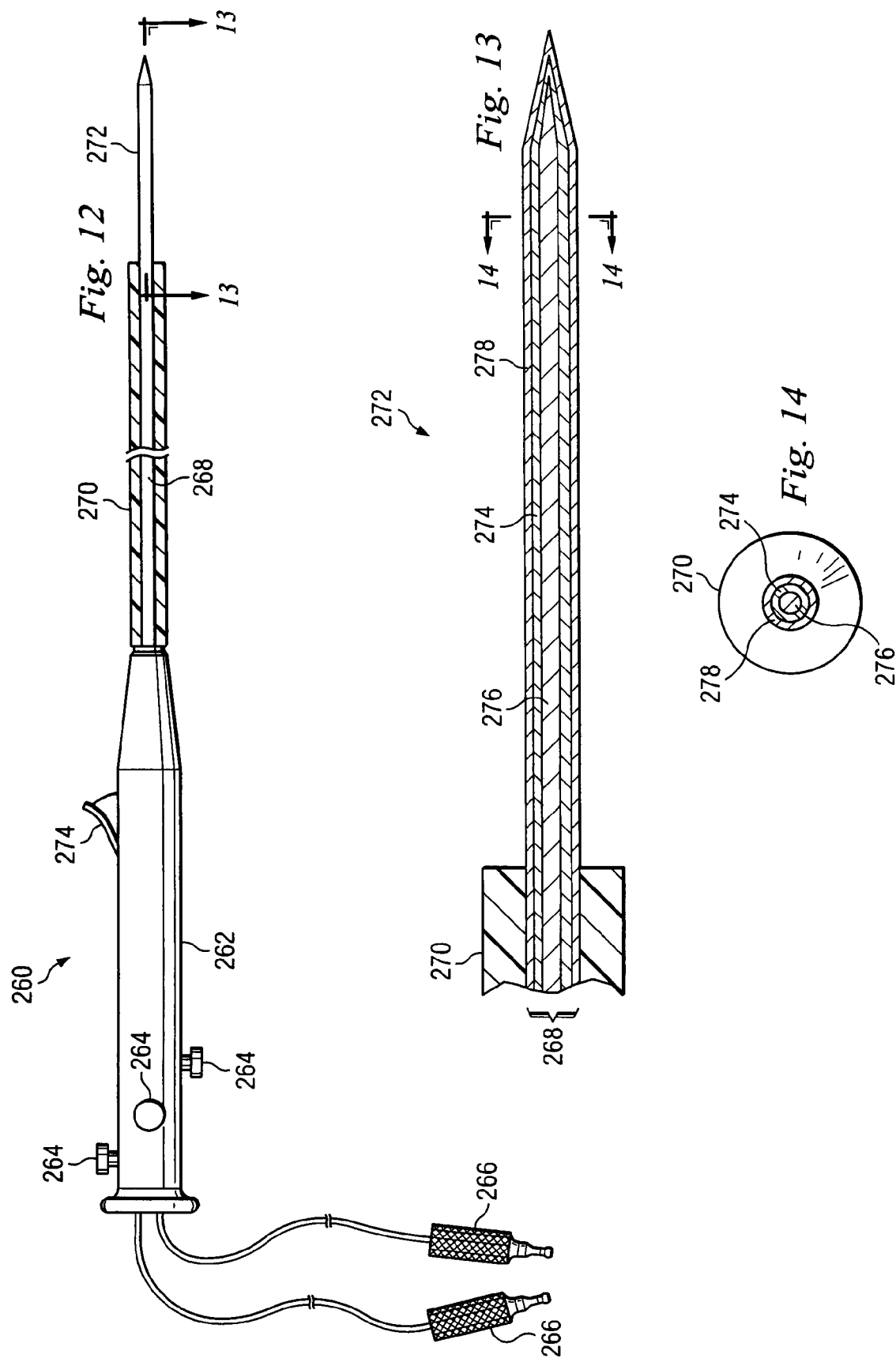

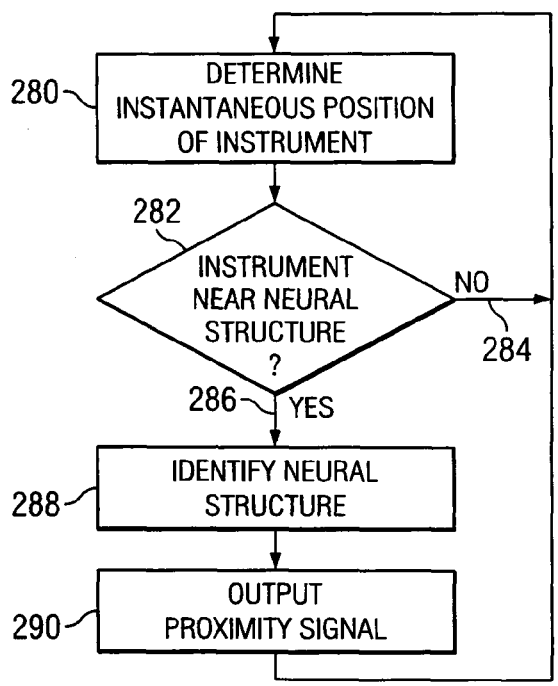
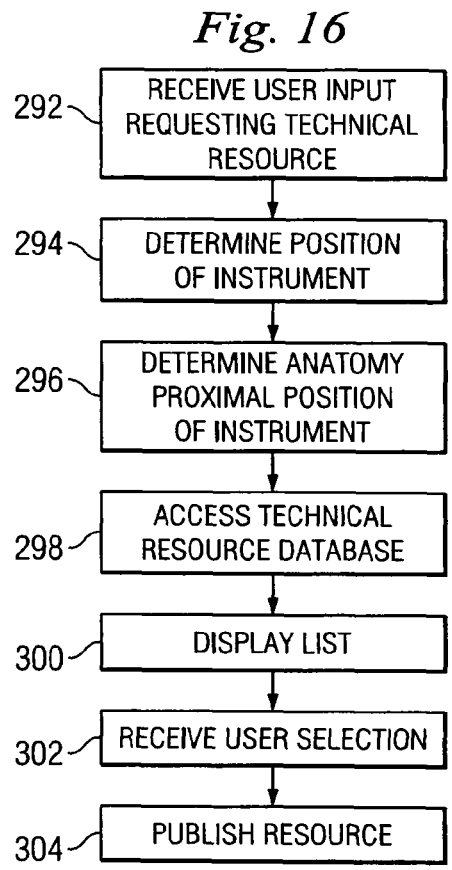
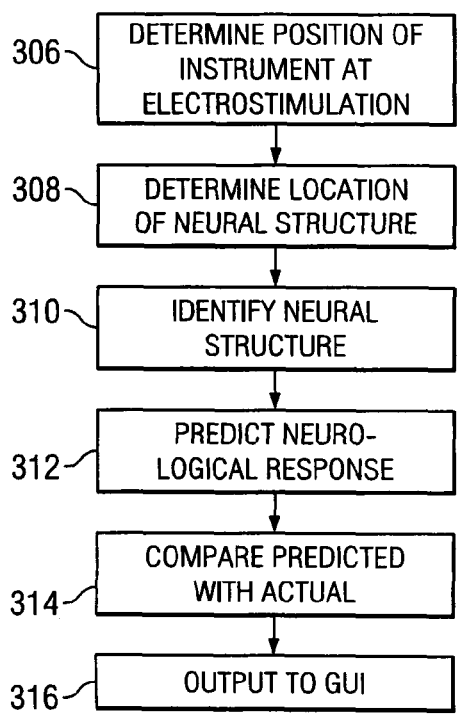

US 7,987,001 B2

SURGICAL NAVIGATIONAL AND NEUROMONITORING INSTRUMENT

BACKGROUND

Surgical procedures and, in particular, neuro-related procedures are often assisted by a surgical navigational system to assist a surgeon in translating and positioning a surgical tool or probe. Conventional surgical navigational systems use reflectors and/or markers to provide positional information of the surgical tool relative to a preoperative rendering of a patient anatomy. Surgical navigational systems, however, do not carry out neuromonitoring functions to determine the integrity of a neural structure or the proximity of the surgical tool to that neural structure. On the other hand, neural integrity monitoring systems are designed to use electrostimulation to identify nerve location for predicting and preventing neurological injury. However, neural integrity monitoring systems do not provide visual navigational assistance. Therefore, there is a need for an integrated neuromonitoring and surgical navigational system that is capable of visually assisting a surgeon in navigating a surgical tool or probe as well as being capable of neuromonitoring to evaluate surgical tool proximity to a neural structure and/or the integrity of the neural structure. There is a further need to have surgical instruments that can apply electrostimulation and be tracked for surgical navigation.

SUMMARY

In one aspect, this disclosure is directed to an apparatus having a surgical tool capable of applying electrostimulation. The surgical tool includes an instrument having a handle portion and a body member extending from the handle portion. The body member has an electrically conductive portion connected to an energy source and is capable of applying electrostimulation energy provided by the energy source. The surgical tool further has a tracking system associated with the instrument and operative to provide information regarding a position of the instrument.

In accordance with another aspect of the present disclosure, a surgical tool assembly is disclosed. The surgical tool assembly includes an instrument having a handle, an insulating sheath, and a conductive member connected to the handle and internal to the insulating sheath. A portion of the conductive member projects distally from the insulating sheath. The surgical tool assembly further has an energy source operable with the instrument and designed to provide electrical energy to the conductive member for application of electrostimulation to a neural structure when the neural structure is in contact with the portion of the conductive member and electrical energy is provided to the conductive member. The surgical tool assembly further has a tracking system associated with the instrument and operative to provide information regarding a position of the instrument.

According to another aspect, the present disclosure is directed to a surgical method that includes inserting a surgical instrument through tissue to a vertebral structure and tracking a position of the surgical instrument relative to the vertebral structure on a user interface. The method further includes delivering an electrical stimulus to the vertebral structure using the surgical instrument and monitoring neurological response to the electrical stimulus.

In accordance with a further aspect, the present disclosure includes a neuromonitoring instrument capable of applying electrostimuation to a neural structure. The instrument has a handle and a stylet extending from a distal end of the handle. The instrument further has a navigational sensor associated with at least one of the handle and the stylet. The navigation sensor is operative to provide feedback regarding a position of the instrument.

These and other aspects, forms, objects, features, and benefits of the present invention will become apparent from the following detailed drawings and descriptions.

BRIEF DESCRIPTION OF THE DRAWINGS

FIG. 7 is a side view of surgical probe according to one aspect of the present disclosure.

FIG. 8 is a side view of a cordless retractor capable of applying electrostimulation according to one aspect of the present disclosure.

FIG. 9 is a side view of a corded retractor capable of applying electrostimulation according to one aspect of the present disclosure.

FIG. 10 is a side view of a cordless bone screwdriver capable of applying electrostimulation according to one aspect of the present disclosure.

FIG. 11 is a side view of a surgical tap capable of applying electrostimulation according to another aspect of the present disclosure.

FIG. 12 is a side view of a surgical probe according to another aspect of the present disclosure.

FIG. 13 is a cross-sectional view of the surgical probe of FIG. 12 taken along lines 13-13 thereof.

FIG. 14 is an end view of the surgical probe shown in FIGS. 12-13.

FIG. 15 is a flow chart setting forth the steps signaling instrument proximity to an anatomical structure according to one aspect of the present disclosure.

FIG. 16 is a flow chart setting forth the steps of accessing and publishing technical resources according to an aspect of the present disclosure.

FIG. 17 is a flow chart setting forth the steps of determining neural structure integrity according to one aspect of the invention.

DETAILED DESCRIPTION

Figure 1:
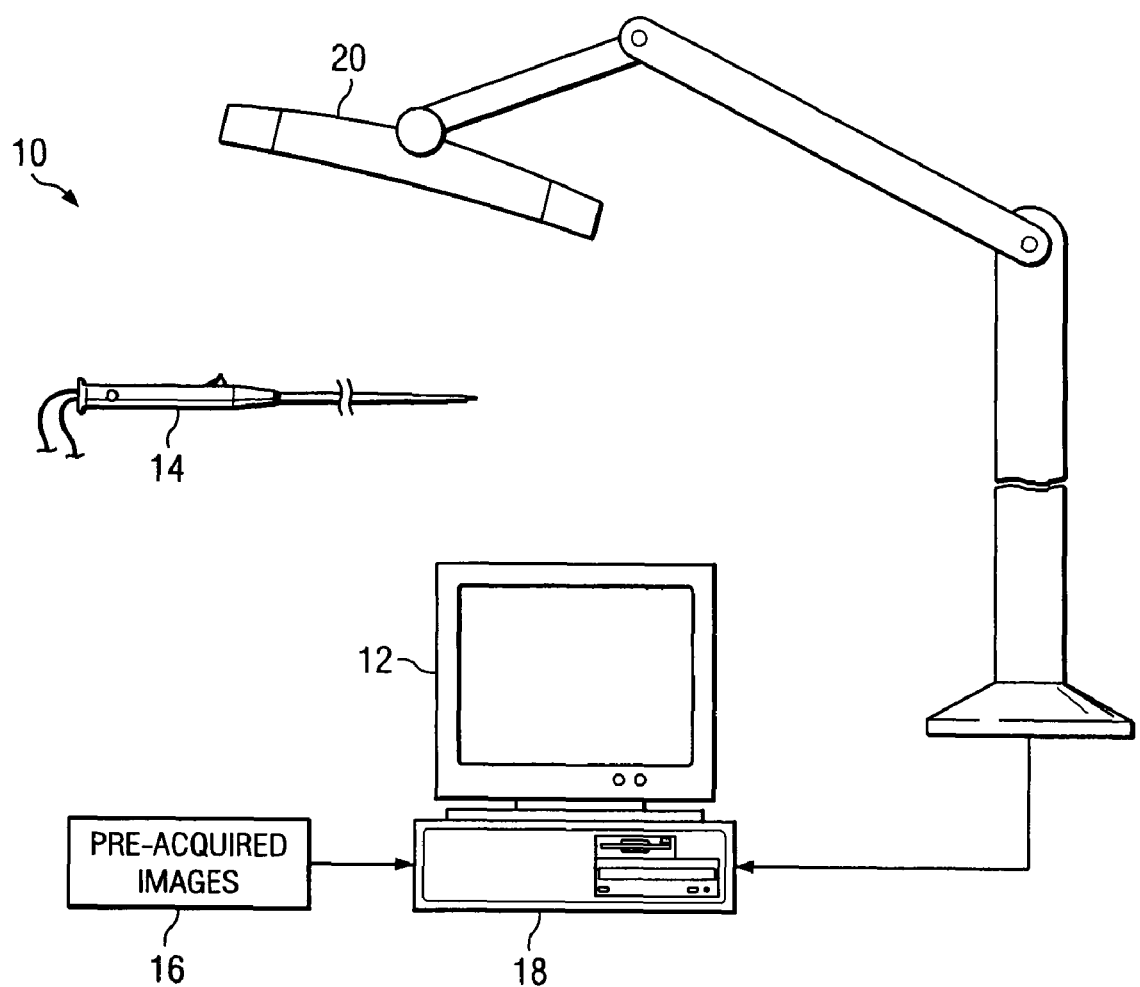
FIG. 1 is a pictorial view of an integrated surgical navigational and neuromonitoring system.

The present disclosure relates generally to the field of neuro-related surgery, and more particularly to systems, instruments, and methods for integrated surgical navigation and neuromonitoring. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

With reference to FIG. 1, there is shown an apparatus for the symbiotic display of surgical navigational and neuromonitoring information to assist a physician in diagnosing and treating various neuro-related conditions. In this regard, a number of surgical procedures can benefit from the present disclosure, such as discectomies, spondy reductions, disc replacements, joint replacements, scoliosis-related procedures, and many others. The integrated image-based surgical navigation and neuromonitoring system 10 enables a surgeon to generate and display on monitor 12 the trajectory of instrument 14, which is preferably a surgical instrument also capable of facilitating the acquisition of neurological information, relative to a visualization of patient anatomy. Data representing one or more pre-acquired images 16 is fed to computer 18. Computer 18 tracks the position of instrument 14 in real-time utilizing detector 20. Computer 18 then registers and displays the trajectory of instrument 14 with images 16 in real-time. An icon representing the trajectory of instrument 14 is superimposed on the pre-acquired images 16 and shown on monitor 12. At the surgeon's command, the real-time trajectory of instrument 14 can be stored in computer 18. This command also creates a new static icon representing the trajectory of the instrument on display 12 at the time the surgeon's command was issued. The surgeon has the option of issuing additional commands, each one storing a real-time trajectory and creating a new static icon for display by default. The surgeon can override this default and choose to not display any static icon. The surgeon also has the option to perform a number of geometric measurements using the real-time and stored instrument trajectories.

In addition to displaying and storing a trajectory of instrument 14 relative to patient anatomy, computer system 18 also updates the visualization of patient anatomy shown on display 12 with indicators representative of neurological information acquired from the patient. As will be described in greater detail below, the neurological indicators can include color coding of certain anatomical structures, textual or graphical annotations superimposed on the pre-acquired images or visualization thereof, or other identifying markers. Reference to a visualization of patient anatomy herein may include a pre-acquired image, a graphical representation derived from one or more pre-acquired images, atlas information, or a combination thereof.

Figure 2:
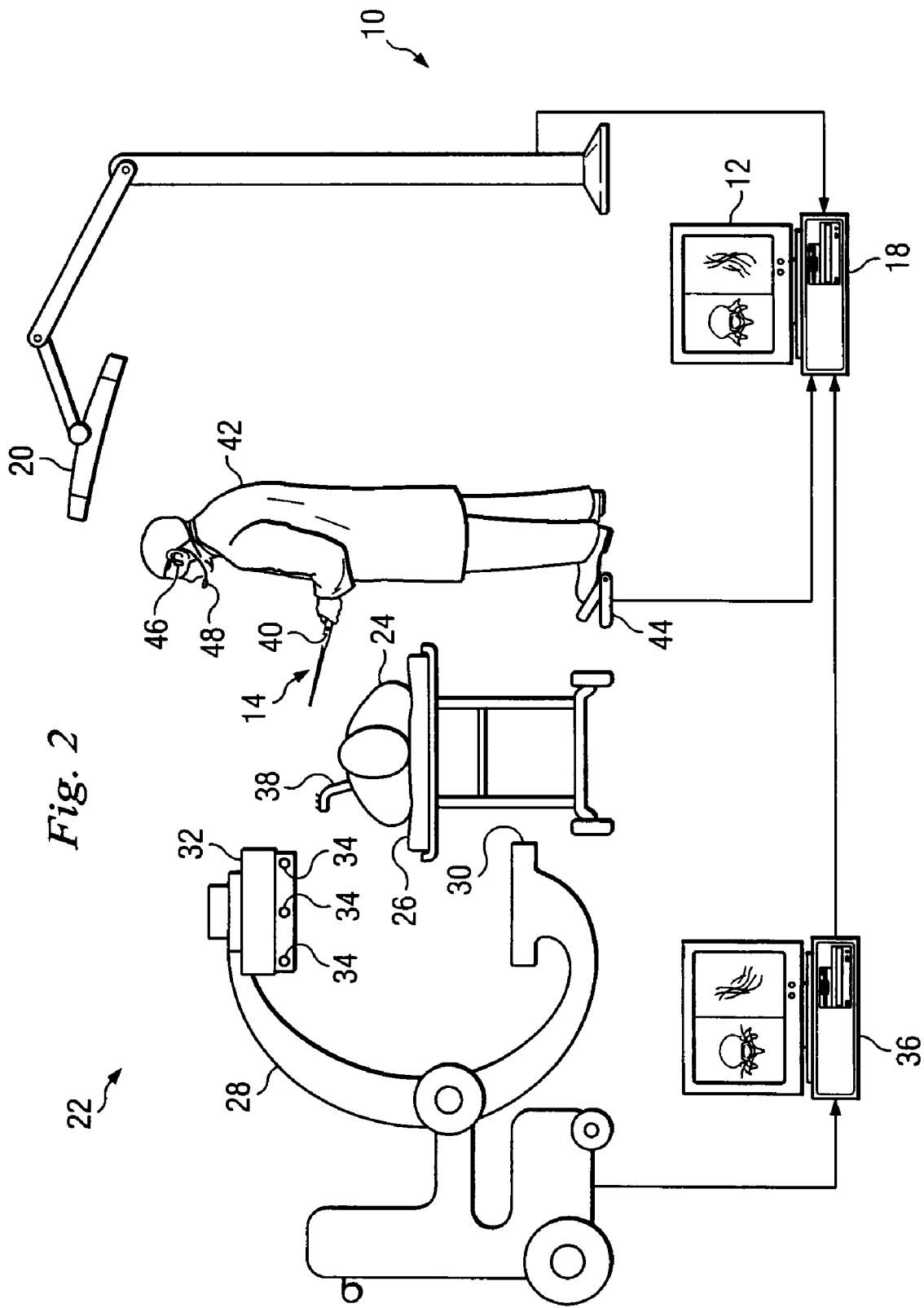
FIG. 2 is a pictorial view of a surgical suite incorporating the integrated surgical navigational and neuromonitoring system of FIG. 1.

Referring to FIG. 2, a surgical suite 22 incorporating the image-based surgical navigation and neuromonitoring system 10 is shown. Pre-acquired images of patient 24 are collected when a patient, lying on table 26, is placed within C-arm imaging device 28. The term "pre-acquired," as used herein, does not imply any specified time sequence. Preferably, however, the images are taken at some time prior to when surgical navigation is performed. Usually, images are taken from two substantially orthogonal directions, such as anterior-posterior (A-P) and lateral, of the anatomy of interest. The imaging device 28 includes x-ray source 30 and x-ray receiving section 32. Receiving section 32 includes target tracking markers 34. Operation of the C-arm imaging device 28 is controlled by a physician or other user by C-arm control computer 36.

While a C-arm imaging device 28 is shown for the acquisition of images from patient 24, it is understood that other imaging devices may be used to acquire anatomical and/or functional images of the patient. For example, images may be acquired using computed tomography (CT), magnetic resonance (MR), positron emission tomography (PET), ultrasound, and single photon emission computed tomography (SPECT). An O-arm imaging system may also be used for image acquisition. Further, it is contemplated that images may be acquired preoperatively with one type of imaging modality remote from the surgical suite 22 and acquired preoperatively or intraoperatively at the surgical suite 22 with another type of imaging modality. These multi-modality images can be registered using known registration techniques.

Acquired images are transmitted to computer 36 where they may be forwarded to surgical navigation computer 18. Computer 18 provides the ability to display the received images via monitor 12. Other devices, for example, such as heads up displays, may also be used to display the images.

Further referring to FIG. 2, system 10 generally performs the real-time tracking of instrument 14, and may also track the position of receiver section 32 and reference frame 38. Detector 20 senses the presence of tracking markers on each object to be tracked. Detector 20 is coupled to computer 18 which is programmed with software modules that analyze the signals transmitted by detector 20 to determine the position of each object in detector space. The manner in which the detector localizes the object is known in the art.

In general, instrument 14 is tracked by the detector, which is part of an optical tracking system (not shown) using attached tracking markers 40, such as reflectors, in order for its three-dimensional position to be determined in detector space. Computer 18 is communicatively linked with the optical tracking system and integrates this information with the pre-acquired images of patient 24 to produce a display which assists surgeon 42 when performing surgical procedures. An iconic representation of the trajectory of instrument 14 is simultaneously overlaid on the pre-acquired images of patient 24 and displayed on monitor 12. In this manner, surgeon 42 is able to see the trajectory of the instrument relative to the patient's anatomy in real-time.

Further referring to FIG. 2, the system according to the invention preferably has the ability to save the dynamic real-time trajectory of instrument 14. By issuing a command using foot-switch 44, for example, computer 18 receives a signal to store the real-time trajectory of the instrument in the memory of computer 18. Alternately, the surgeon or other user may issue the command using other input devices, such as a push-button on the instrument, voice command, touchpad/touch screen input, and the like. This "storage command" also instructs computer 18 to generate a new static icon representing the saved trajectory of the instrument, essentially "freezing" the icon at the point when the input was received. The static icon, along with the icon representing the real-time trajectory of the instrument, can be simultaneously superimposed over the pre-acquired image. If multiple images are being displayed, both static and real-time icons can be superimposed on all of the displayed images. Other means of issuing the storage command, such as, for example, through a GUI, may also be used. The surgeon also has the option of storing multiple instrument trajectories. Each time a desired storage command is issued, the real-time trajectory of the instrument is stored and a new static icon representing the stored trajectory is displayed on the pre-acquired image, or if more than one image is being displayed, on all the pre-acquired images.

The system according to the invention preferably has the additional capability to measure angles between the real-time trajectory and one or more of the stored trajectories, or between stored trajectories, in a manner similar to that described in U.S. Pat. No. 6,920,347, the disclosure of which is incorporated herein.

In addition to tracking and storing instrument trajectory, as will be described, neurological information can be acquired from the patient and that information that can be represented in a visible form that can be shown on display 12. For example, with the aid of pre-acquired images and trajectory information, surgeon 42 may move the instrument 14 in a guided manner to an anatomical region containing neural structures and using instrument 14 or other neurologically stimulating device together with electrodes (not shown) may then acquire neurological information from the neural structures. The acquired neurological information is then passed to computer 18 which registers the neurological information with the neural structure from which the neurological information was acquired. Based on the position of the instrument 14, computer 18 can determine the location of the neural structure that was stimulated and then update the visualization of that neural structure on display 12 to include markers or other indices representative of the acquired neurological information. For example, based on the location, orientation, and neurological response, computer 18 can determine the class of the stimulated neural structure and add an annotation to the visualization of the neural structure on display 12. Alternately, the neural structure may be assigned a designated color in the visualization on display 12 based on its class or other defining characteristics.

In addition to characterizing a stimulated neural structure, computer 18, together with positional information of the neural structure, may also predict the structure of the nerve and graphically display that predicted structure to the surgeon on display 12. In this regard, a portion of a nerve may be stimulated, but the entire nerve structure predicted and graphically displayed. Further, while the pre-acquired images and/or visualizations thereof provide the surgeon with a general understanding of the patient anatomy relative to the tracked instrument, the acquired neurological information supplements that understanding with greater precision with respect to neural structures. Thus, by localizing the position of neural structures, the integrated system enhances the surgeon's understanding of the anatomy for the particular patient. To further assist the surgeon, through localization of neural structures, viewable or audible indicators may be automatically given by the computer 18 to the surgeon when the instrument 14 is in proximity to a neural structure. Moreover, the indicators may be tailored to coincide with the class, position, or other characteristic of the neural structure.

Using voice recognition software and hardware, or other input devices, surgeon 42 or other user may also add notes regarding the neural structure from which a neurological response was measured. Those notes may then be stored in memory of computer 18. In one embodiment, surgeon 42 wears a headphone 46 and microphone 48 to facilitate hands-free note making during the surgical procedure. As will be explained further below, computer 18 may also broadcast on-demand audio information to the surgeon via an audio system connected to the headphone or other speakers.

Figure 3:
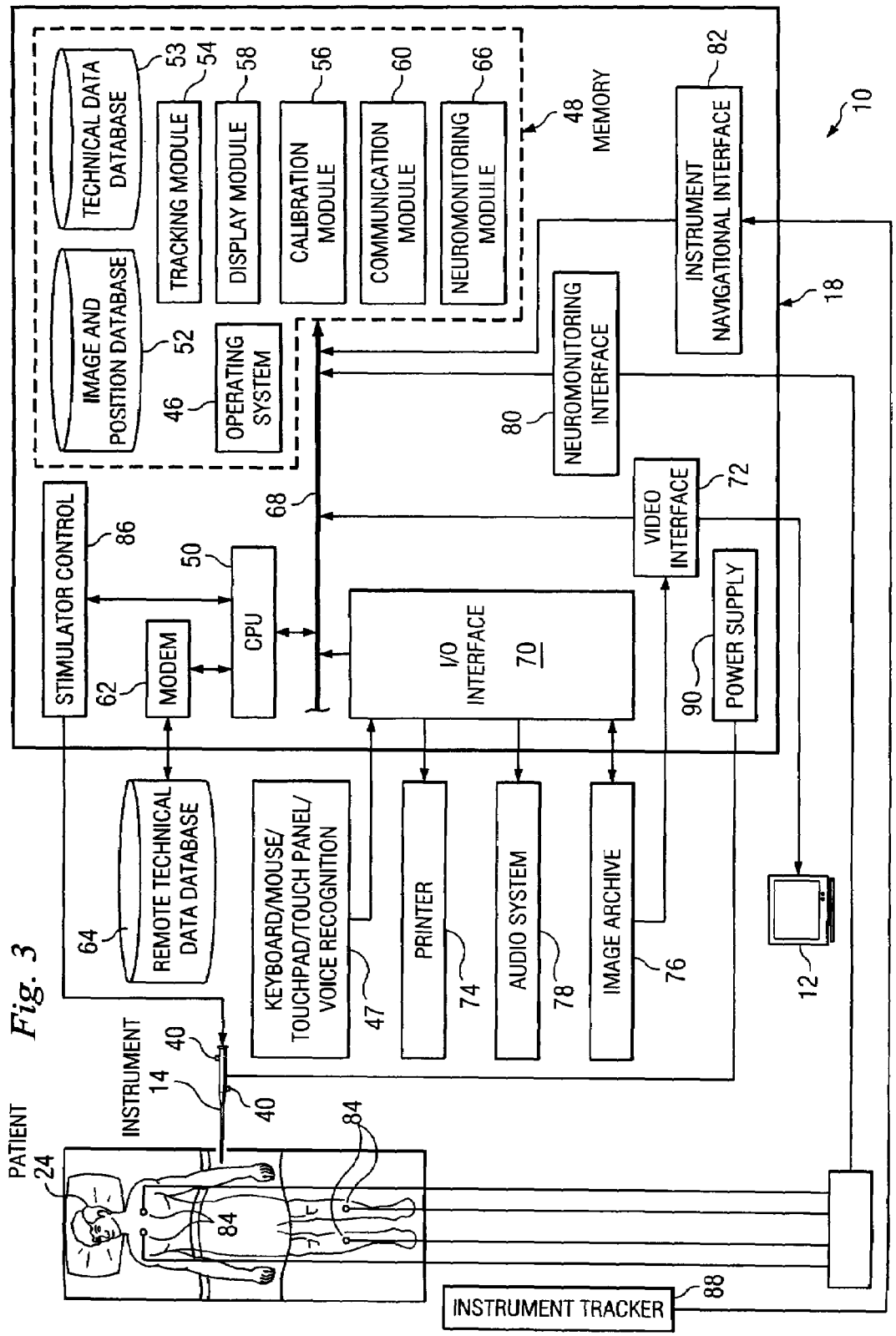
FIG. 3 is a block diagram of the integrated surgical navigational and neuromonitoring system of FIG. 1.

Referring now to FIG. 3, a block diagram of the integrated surgical navigational and neuromonitoring system 10 is shown. Computer 18 includes a GUI system operating in conjunction with a display screen of display monitor 12. The GUI system is implemented in conjunction with operating system 46 running computer 18. The GUI is implemented as part of the computer 18 to receive input data and commands from a user interface 47 such as a keyboard, mouse, light-wand, touchpad, touch screen, voice recognition module, foot switch, joystick, and the like. For simplicity of the drawings and explanation, many components of a conventional computer have not been illustrated such as address buffers, memory buffers, and other standard control circuits because these elements are well known in the art and a detailed description thereof is not necessary for understanding the present invention.

A computer program used to implement the various steps of the present invention is generally located in memory unit 48, and the processes of the present invention are carried out through the use of a central processing unit (CPU) 50. The memory unit 48 is representative of both read-only memory and random access memory. The memory unit also contains a database 52 that stores data, for example, image data and tables, including such information as stored instrument positions, extension values, and geometric transform parameters, used in conjunction with the present invention. Database 52 can also be used to store data, such as quantitative and qualitative assessments, of monitored neurological structures. The memory unit further contains a technical data database 53 that stores data pertaining to, for example, surgical procedures, general anatomical structure information, videos, publications, tutorials, presentations, anatomical illustrations, surgical guides, and the like, that can be accessed by a surgeon or other user preoperatively, intraoperatively, or postoperatively to assist with diagnosis and treatment. Also contained in memory 48 is a communication software module 60 that facilitates communication, via modem 62, of the computer 18 to remote databases, e.g., technical data database 64.

It is understood that the single representations of an image archival database and a technical data database is for demonstrative purposes only, and it is assumed that there may be a need for multiple databases in such a system. Additionally, computer 18 may access the databases via a network (not shown). According to the present invention, any acceptable network may be employed whether public, open, dedicated, private, or so forth. The communications links to the network may be of any acceptable type, including conventional telephone lines, fiber optics, cable modem links, digital subscriber lines, wireless data transfer systems, or the like. In this regard, the computer 18 is provided with communications interface hardware 62 and software 60 of generally known design, permitting establishment of networks links and the exchange of data with the databases.

CPU 50, in combination with the computer software comprising operating system 46, tracking software module 54, calibration software module 56, display software module 58, communication module 60, and neuromonitoring software module 66 controls the operations and processes of system 10. The processes implemented by CPU 50 may be communicated as electrical signals along bus 68 to an I/O interface 70 and a video interface 72. In addition to be connected to user interface 47, the I/O interface is connected to a printer 74, an image archive (remote or local) 76, and an audio (speaker) system 78.

Tracking software module 54 performs the processes necessary for tracking objects in an image guided system as described herein and are known to those skilled in the art. Calibration software module 56 computes the geometric transform which corrects for image distortions and registers the images to the anatomical reference frame 38, and thus the patient's anatomy.

Display software module 58 applies, and if desired, computes the offsets between the guide tracking markers 40 and the instrument 14 in order generate an icon representing the trajectory of the instrument for superposition over the images. For instruments with fixed lengths and angulations, these offsets can be measured once and stored in database 52. The user would then select from a list of instruments, the one being used in the procedure so the proper offsets are applied by display software module 58. For instruments with variable lengths and angulations, the offsets could be measured manually and entered via keyboard 47, or measured in conjunction a tracked pointer (not shown) or tracked registration jig (not shown).

Pre-acquired image data stored locally in image database 52 or remotely in image archive 76 can be fed directly into computer 18 digitally through I/O interface 70, or may be supplied as video data through video interface 72. In addition, items shown as stored in memory can also be stored, at least partially, on a hard disk (not shown) or other memory device, such as flash memory, if memory resources are limited. Furthermore, while not explicitly shown, image data may also be supplied over a network, through a mass storage device such as a hard drive, optical disks, tape drives, or any other type of data transfer and storage devices.

In addition to the modules and interfaces described above, computer 18 includes a neuromonitoring interface 80 as well as an instrument navigation interface 82. The neuromonitoring interface 80 receives electrical signals from electrodes 84 proximate patient 24. The electrical signals are detected by electrodes 84 in response to electrostimulation applied to neural structures of the patient by instrument 14 or other electrostimulating probe (not shown). In this example, the electrodes are electromyography (EMG) electrodes and record muscle response to nerve stimulation. Alternately, other neuromonitoring techniques, such as, motor evoked potentials (MEP) neuromonitoring and somatosensory evoked potentials (SSEP) neuromonitoring, may be used. A stimulator control 86 interfaces with instrument 14 and controls the intensity, direction, and pattern of stimulation applied by instrument 14. Inputs establishing desired stimulation characteristics may be received by the surgeon or other user via input interface 47 or on the instrument 14 itself.

As described above, the integrated system 10 also carries out real-time tracking of instrument 14 (and patient 24) using markers, reflectors, or other tracking devices. Alternately, the instrument may include active devices such as signal emitters that communicate with tracking equipment to determine a position or orientation of the instrument. For example, the emitter may emit infrared, RF, or other signals for tracking of the instrument. In one example, instrument 14 includes markers 40 whose movements are tracked by instrument tracker 88, which may include a camera or other known tracking equipment. Similarly, the patient may include markers or reflectors so that patient movement can be tracked. To effectuate application of an electrical stimulus, instrument 14 is also connected to a power supply 90. As will be shown, the instrument 14 may be powered by a battery housed within the instrument itself, a power supply housed within the computer cabinet, or inductively. Thus, if active devices, such as emitter or transmitters are used for tracking these devices can be similarly powered.

The integrated surgical navigational and neuromonitoring system is designed to assist a surgeon in navigating an instrument, e.g., surgical tool, probe, or other instrument, through visualization of the instrument relative to patient anatomy. As described herein, using tracking tools and techniques, real-time positional and orientation information regarding the instrument relative to patient anatomy can be superimposed on an anatomical, functional, or derived image of the patient. In addition to assisting a surgeon with instrument tracking, the integrated system 10 also performs neuromonitoring to assess the position and integrity of neural structures. In this regard, the surgeon can move the instrument to a desired location, view the placement of the instrument relative to patient anatomy on display 12, apply an electrical stimulus to neural structures proximate the instrument, and measure the response to that electrical stimulus. This neural information gathered can then be added to the visualization of the patient anatomy through graphic or textual annotations, color or other coding of the neural structure, or other labeling techniques to convey, in human discernable form, the neural information gathered from the application of an electrical stimulus. The integrated system also helps the surgeon in visualizing patient anatomy, such as key nerve structures, and associating position or integrity with the patient anatomy. As will be shown with respect to FIGS. 4-5, a GUI is used to convey and facilitate interaction with the surgical navigational and neuromonitoring information.

Figure 4:
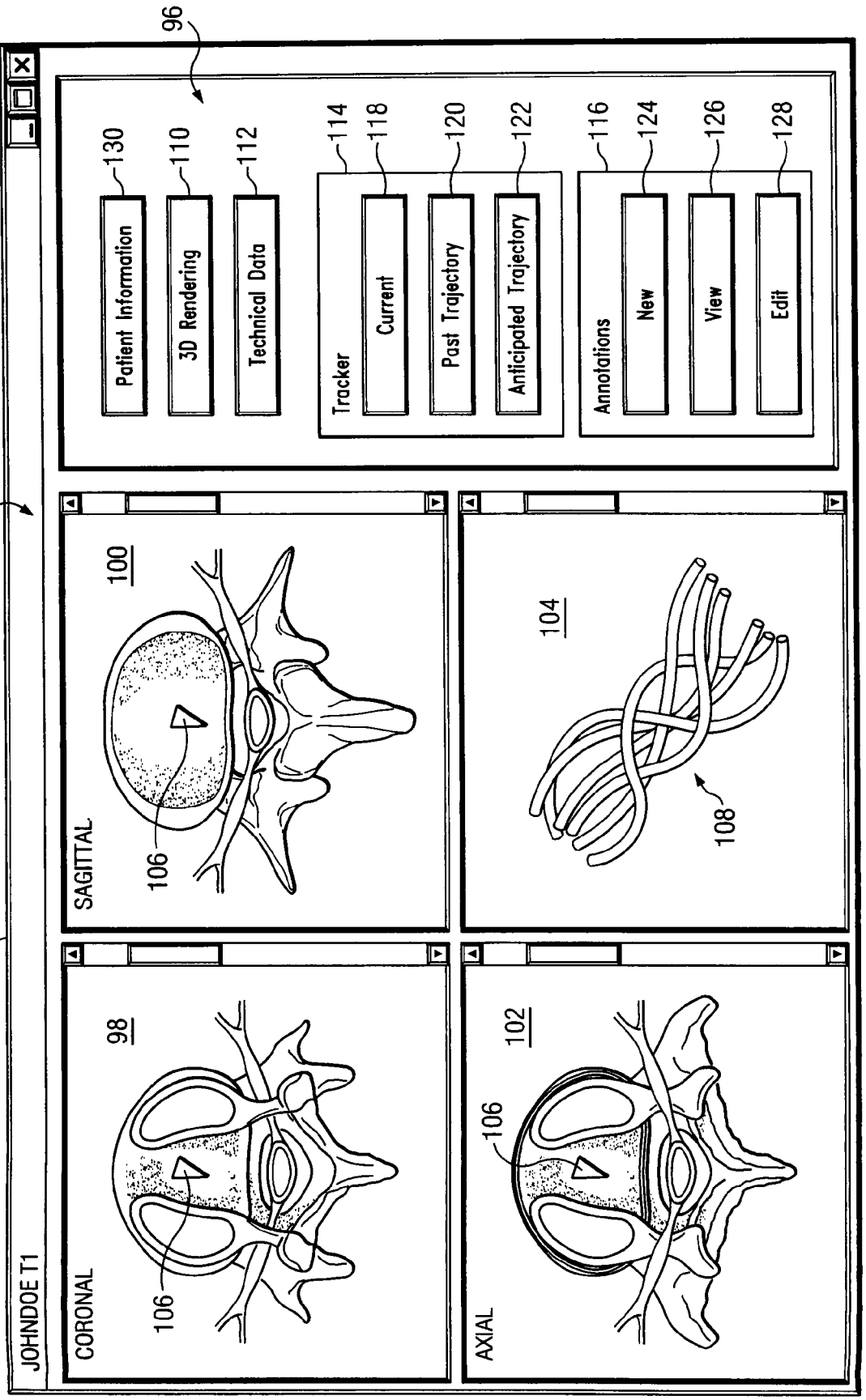
FIG. 4 is a front view of a GUI displayed by the integrated surgical navigational and neuromonitoring system of FIGS. 1-3.

Referring now to FIG. 4, a GUI 92 designed to assist a surgeon or other user in navigating a surgical tool, such as a probe or a bone screwdriver, is shown. In the illustrated example, the GUI 92 is bifurcated into an image portion 94 and a menu portion 96. The image portion contains three image panes 98, 100, 102 that, in the illustrated example, contain a coronal, a sagittal, and an axial image, respectively, of patient anatomy. The image portion also contains a rendering pane 104. The menu portion 96 provides selectable links that, when selected by a surgeon, enables interfacing with that displayed in the image panes 98, 100, 102 or with other data acquired from the patient.

The image panes provide an anatomical map or framework for a surgeon to track an instrument, which can be representatively displayed by pointer 106. The integrated system described herein tracks movement of an instrument and provides a real-time visualization of the position of the pointer superimposed on the images contained in panes 98, 100, 102. It is noted that the displayed images can be derived from one or more diagnostic images acquired of the patient, an atlas model, or a combination thereof. As the instrument is moved relative to the patient anatomy, the images displayed in the image panes are automatically refreshed such that an instantaneous position of the instrument, via pointer 106, provides positional information to the surgeon.

Moreover, as the integrated system supports both surgical instrument navigation and neuromonitoring, the image panes and the positional feedback provided by pointer 106 can assist the surgeon in isolating a neural structure for neural monitoring. That is, a general understanding of nerve location can be determined from the images contained in the image panes 98, 100, 102. Through visual inspection of the panes, the surgeon can then move the instrument proximal a neural structure, apply an electrostimulation, and measure the neurological response. That neurological response can be used to assess the integrity of the neural structure in a manner consistent with known neuromonitoring studies. Additionally, the neurological information can also be used to localize more precisely the position of the stimulated neural structure. For example, the visualization of patient anatomy, e.g., the images contained in panes 98, 100, 102, provides a general visual understanding of anatomy position, orientation, and location. The neurological response of a stimulated neural structure can then be used to pinpoint the position and orientation of that neural structure on the patient anatomy visualization using color-coding or other indicia.

Moreover, based on the general location of a neural structure and its localized position, assessment of the neural structure can be enhanced. That is, the computer, using the measured response of a neural structure and its positional information, as indicated by the surgeon positioning the instrument proximal the structure, can compare the measured response to data contained in a database and determine if the measured response is consistent with that expected given.

In addition to integrity assessment and positional localization, the integration of the navigation and neuromonitoring information enables the development of neural maps. That is, through repeated movement of the instrument and neurological monitoring, the combined information can be integrated to localize neural structure position, classify those neural structures based on position and/or response, and code through color or other indicia, a neurological, anatomically driven map of the patient.

It is noted that in the illustrated example, the tip of the instrument is represented by pointer 106. However, it is contemplated that tip, hind, or full instrument representations can be used to assist with navigation. Also, while three images of the same anatomy, but at different views are shown, other image display approaches may be used.

Still referring to FIG. 4, one of the image panes 104 is illustratively used for a three-dimensional rendering of a patient anatomy, such as a neural structure bundle 108. The rendering can be formed by registration of multi-angle images of the patient anatomy, derived from atlas information, or a combination thereof. In practice, the surgeon positions the instrument proximal a target anatomical structure. The surgeon then, if desired, selects "3D Rendering" tab 110 of menu 96. Upon such a selection, the computer than determines the position of the pointer 106 and generates a 3D rendering of the anatomical structure "pointed at" by the pointer. In this way, the surgeon can select an anatomical feature and then visually inspect that anatomical feature in a 3D rendering on the GUI 92.

Further, as referenced above, the integrated system maintains or has access to a technical library contained on one or more databases. The surgeon can access that technical data through selection of "Technical Data" tab 112. Upon such a selection, the computer causes display of available resources (not shown) in menu 96. It is contemplated that another window may be displayed; however, in a preferred implementation, a single GUI is used to prevent superposition of screens and windows over the navigational images. The technical resources may include links to internet web pages, intranet web pages, articles, publications, presentations, maps, tutorials, and the like. Moreover, in one preferred example, the list of resources is tailored to the given position of the instrument when the surgeon selects tab 112. Thus, it is contemplated that access to the technical resource information can be streamlined for efficient access during a surgical procedure.

Menu 96 also includes a tracker sub-menu 114 and an annotation sub-menu 116. The tracker sub-menu 114, in the illustrated example, includes a "current" tab 118, a "past trajectory" tab 120, and an "anticipated trajectory" tab 122 that provide on-demand view options for displaying instrument navigation information. User selection of tab 118 causes the current position of the instrument to be displayed in the image panes. User selection of tab 120 causes the traveled trajectory of the instrument to be displayed. User selection of tab 122 causes the anticipated trajectory, based on the current position of the head of the instrument, to be displayed. It is contemplated that more than a single tab can be active or selected at a time.

The annotations sub-menu 116 contains a "New" tab 124, a "View" tab 126, and an "Edit" tab 128. Tabs 124, 126, 128 facilitate making, viewing, and editing annotations regarding a surgical procedure and anatomical and neural observations. In this regard, a surgeon can make a general annotation or record notes regarding a specific surgical procedure or anatomical observation, such as an observation regarding a neural structure, its position, integrity, or neurological response. In one preferred example, the computer automatically associates an annotation with the position of the instrument when the annotation was made. Thus, annotations can be made and associated with a neural or other structure during the course of a surgical procedure. Moreover, by depressing the "view" tab 126, the computer will cause a list of annotations to be appear in pane 116. Alternately, or in addition thereto, annotations made and associated with a neural structure will be viewable by positioning the instrument proximal the neural structure. Akin to a mouse-over technique, positioning the instrument proximal an annotated neural structure will cause any previous annotations to appear automatically if such a feature is enabled.

It is understood that other tabs and selectors, both general, such as a patient information tab 130, or specific, can be incorporated into the menu pane 96. It is also understood that the presentation and arrangement of the tabs in menu pane 96 is merely one contemplated example.

Figure 5:
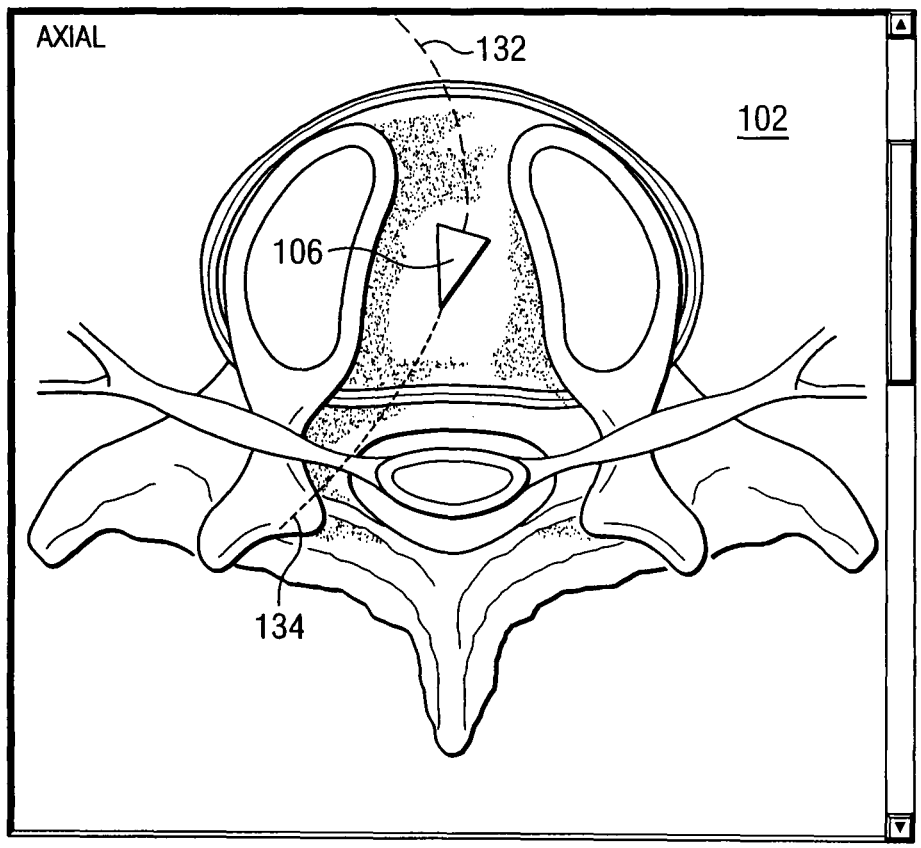
FIG. 5 is a front view of a portion of the GUI shown in FIG. 4.

Referring now to FIG. 5, image pane 102 is shown to further illustrate instrument tracking. As described above, through user selection of the appropriate input tab, the instantaneous position of the instrument can be viewed relative to patient anatomy via localization of pointer 106. Additionally, selection of the "past trajectory" tab 120 on menu 96, FIG. 4, causes the past or traveled trajectory of the instrument to be shown by dashed trajectory line 132. Similarly, the anticipated trajectory 134 can also be viewed relative to the patient anatomy based on the instantaneous position and orientation of the tip or leading portion of the instrument.

Additionally, it is contemplated that trajectory paths can be stored and that stored trajectories can be recalled and viewed relative to the patient anatomy. In this regard, a current or real-time instrument trajectory can be compared to past trajectories. Moreover, it is recognized that not all instrument movement is recorded. In this regard, the surgeon or other user can turn instrument tracking on and off as desired. Also, although the look-ahead technique described above projects the graphical representation of the instrument into the image, there is no requirement that the instrument's graphical representation be in the space of the image to be projected into the image. In other words, for example, the surgeon may be holding the instrument above the patient and outside the space of the image, so that the representation of the instrument does not appear in the images. However, it may still be desirable to project ahead a fixed length into the image to facilitate planning of the procedure.

In the illustrated example, a trajectory is represented by a directional line. It is contemplated, however, that other representations may be used. For example, a trajectory can be automatically assigned a different color or unique numerical label. Other types of directional indicators may also be used, and different shapes, styles, sizes, and textures can be employed to differentiate among the trajectories. The surgeon also has the option of not showing the label for any trajectory if desired. The surgeon also has the option of changing the default color or label text for any trajectory through appropriate controls contained in menu 96. In one example, past trajectories are assigned one color whereas anticipated or look-ahead trajectories are assigned a different color. Also, while on a single trajectory is illustrated in FIG. 5, it is recognized that multiple instruments can be tracked at a time and their trajectories tracked, predicted, and displayed on the image.

As described with respect to FIGS. 1-5, the integrated system 10 tracks the position of an instrument, such as a surgical tool or probe, relative to patient anatomy using markers, reflectors, and the like. In one aspect, the instrument is also capable of applying an electrical stimulus to a neural structure so that neurological information, such as nerve position and nerve integrity, can be determined without requiring introduction of another instrument to the patient anatomy. The instrument can be tethered to a computer 18 via a stimulator control interface 86 and a power supply 90, or, in an alternate embodiment, the instrument can be wirelessly connected to the stimulator control interface 86 and be powered inductively or by a self-contained battery.

Figure 6:
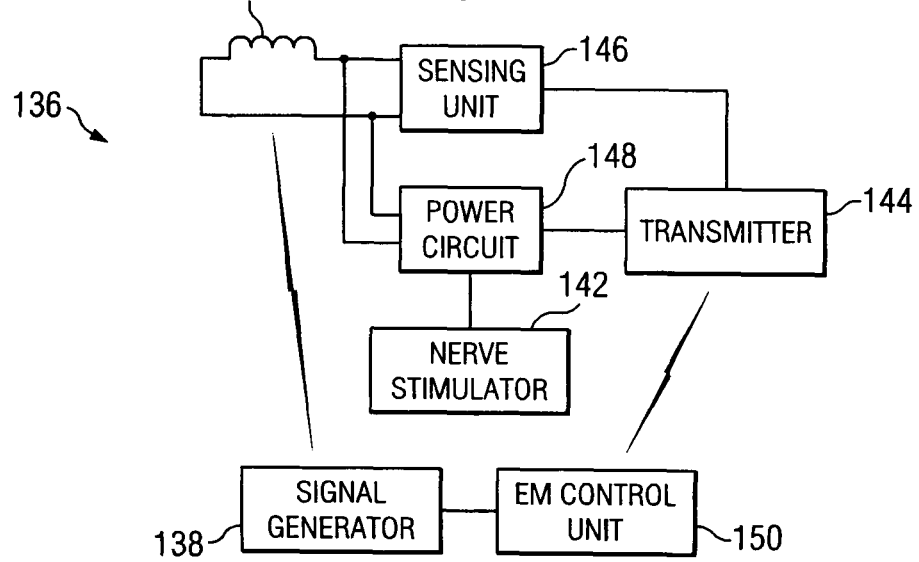
FIG. 6 is a block diagram of a wireless instrument tracking system for use with the integrated surgical navigational and neuromonitoring system of FIGS. 1-3.

FIG. 6 illustrates operational circuitry for inductively powering the instrument and for wirelessly determining positional information of an instrument rather than using markers and reflectors. The operational circuitry 136 includes a signal generator 138 for generating an electromagnetic field. The signal generator 138 preferably includes multiple coils (not shown). Each coil of the signal generator 138 may be activated in succession to induce a number of magnetic fields thereby inducing a corresponding voltage signal in a sensing coil.

Signal generator 138 employs a distinct magnetic assembly so that the voltages induced in a sensing coil 140 corresponding to a transmitted time-dependent magnetic field produce sufficient information to describe the location, i.e. position and orientation, of the instrument. As used herein, a coil refers to an electrically conductive, magnetically sensitive element that is responsive to time-varying magnetic fields for generating induced voltage signals as a function of, and representative of, the applied time-varying magnetic field. The signals produced by the signal generator 138 containing sufficient information to describe the position of the instrument are referred to hereinafter as reference signals.

The signal generator is also configured to induce a voltage in the sensing coil 140 sufficient to power electronic components of the instrument, such as a nerve stimulation unit 142 and a transmitter 144. In the preferred embodiment, the signals transmitted by the signal generator 138 for powering the device, hereinafter referred to as powering signals, are frequency multiplexed with the reference signals. The frequency ranges of the reference signal and powering signal are modulated so as to occupy mutually exclusive frequency intervals. This technique allows the signals to be transmitted simultaneously over a common channel, such as a wireless channel, while keeping the signals apart so that they do not interfere with each other. The reference and positional signals are preferably frequency modulated (FM); however, amplitude modulation (AM) may also be used.

Alternatively, the powering signals may be transmitted by separate signal generators, each at a differing frequencies. As embodied herein, the portion for receiving a reference signal further includes a sensing unit 146 and a power circuit 148. Sensing unit 146 and power circuit 148 each may receive an induced voltage signal due to a frequency multiplexed reference signal and powering signal on sensing/powering coil 140. Sensing unit 146 and power circuit 148 both may separate the voltage signals induced by the multiplexed magnetic signals into positional and powering signals.

The sensing unit 146 measures the induced voltage signal portion corresponding to a reference signal as a positional signal indicative of a current position of the instrument. The positional signal is transmitted by transmitter 144. Similarly, power circuit 148 may retain the induced voltage signal portion corresponding to a powering signal for producing power sufficient to power the transmitter 144 and apply electrostimulation to a neural structure. Power circuit 148 rectifies the induced voltage generated on the coil 140 by the powering signals to produce DC power that is used power the transmitter 144 and the nerve stimulation unit 142. Power circuit 148 may store the DC power using a capacitor, small battery, or other storage device for later use.

The integrated system 10 includes an electromagnetic control unit 150 that regulates operation of the signal generator 138 and includes a receiver (not shown) for receiving the positional information transmitted wirelessly by the transmitter 144. In this regard, the control unit 150 is adapted to receive magnetic field mode positional signals and transmit those positional signals to the CPU for processing to determine the position and/or orientation of the instrument. The CPU preferably begins determining the position of the instrument by first determining the angular orientation of the sensing coil 140 and then using the orientation of the coil 140 to determine the position of the instrument. However, the present invention is not limited to any specific method of determining the position of the instrument. While a single sensing/powering coil 140 is shown, it is contemplated that separate sensing and powering coils may be used.

As described herein, in one aspect of the disclosure, a surgical instrument, such as a probe, a retractor, or a bone screwdriver is also used to apply an electrical stimulus to a neural structure. In addition to applying electrostimulation, the surgical instruments can be equipped with appropriate circuitry and controls to remotely control the neuromonitoring and navigational system. FIGS. 7-14 and 18 illustrate various examples of integrated surgical and electro stimulating tools.

FIG. 7 illustrates a surgical probe 152 that includes an elongated and, preferably, textured handle 154 having a proximal end 156 and a distal end 158. The surgical probe 152 is connectable to the neuromonitoring interface 80, FIG. 3, by jacks 160 extending from the handle proximal end 156. Handle includes a transversely projecting actuator 162 proximate a tapered distal segment 164 terminating in handle distal end 158 which carries a distally projecting stainless steel shaft 166. Shaft 166 is tapered and preferably has a larger outside diameter proximate the handle distal end 158, tapering to a smaller outside diameter proximate the shaft distal end 168, with a distally projecting length from handle distal end 158 to shaft distal end 168 encased in clear plastic, thin-wall, shrinkable tubing. Extending from the handle 154 and electrically connected to conductors 170 is an anode 172 and a cathode 174. The anode and cathode 172, 174 extend slightly past the shaft distal end 168 and are used to apply electrostimulation to a neural structure.

The outer surface of the handle 154 also includes a reflector/marker network 176 to facilitate tracking of the position and orientation of the probe 152. The probe 152 is shown as having three reflectors 176 that may be permanently or removably fixed to the handle 154. As is known in conventional surgical instrument tracking systems, the size, shape, and position of the reflectors 176 are known by the surgical navigational system, thus, when captured by a camera, the position and orientation of the probe 152 can be readily ascertained. It is recognized that more than or less than three reflectors may be used.

The actuator 162 enables the surgeon to selectively apply electrostimulation to patient anatomy during a surgical procedure. As such, the probe 152 can be used for surgical purposes without the application of electrostimulation and, when desired by the surgeon, used to illicit a neurological response from a neural structure. In the embodiment illustrated in FIG. 7, the probe 152 is powered by a power supply (not shown) external to the probe 152 via the jacks 160.

In FIG. 8, a battery powered retractor according to another embodiment of the invention is shown. Retractor 178 includes elongated and, preferably, textured handle 180 having a proximal end 182 and a distal end 184. Extending from the distal end 184 is a tapered shaft 186 that terminates in a curved head 188 that includes an anode tip 190 and a cathode tip 192, that are coplanar with one another. The handle 180 provides an interior volume 194 sized and shaped to hold batteries 196 that supply power sufficient to electrostimulate neural structures when desired by the surgeon. In one embodiment, the batteries 196 are permanently sealed within the interior volume 194 of the handle 180 so as to prevent contact with body fluids and cleaning fluids. In another embodiment, not illustrated herein, the batteries are removable and therefore replaceable by threadingly removing a cap portion of the handle. It is contemplated that rechargeable batteries may be used and that the batteries may be recharged without removing them from the handle.

The handle 180 also includes three reflectors 198 that provide visual feedback to a camera (not shown) or other detection device to determine the position and orientation of the retractor. Similar to that described with respect to FIG. 7, the retractor 178 further includes an actuator 200 that enables a surgeon to selectively turn the electrostimulation functionality of the retractor 178 on so as to apply electrostimulation to a neural structure.

FIG. 9 illustrates a corded retractor 202 according to the present disclosure. In this example, the retractor 202 is powered by a remote battery or other power supply through a conventional jack connection using jacks 204. Like that described with respect to FIG. 8, the handle 206 of the retractor 202 includes reflectors 208 to enable surgical navigational hardware and software to track the position and orientation of the retractor 202. Retractor 202 also includes an actuator 210 to selectively apply electrostimulation to a neural structure. Electrostimulation is facilitated by an anode conductor 212 and a cathode conductor 214 extending past the shaft 216. The anode and cathode conductors 212, 214 extend along the entire length of the shaft 216 and connect to a power supply via connection with jack connectors 217.

For both retractor examples it is contemplated that the position and orientation of a retractor can be monitored and, accordingly, the retractor can be opened and closed automatically to prevent neuron-related damage by extended retraction.

In another example, as shown in FIG. 10, a bone screwdriver 218 is configured to provide electrostimulation in addition to driving a bone screw. Screwdriver 218 includes a handle 220 with a driving shaft 222 extending from a distal end thereof. The handle 220 is sized to accommodate batteries 224 to provide power for electrostimulation. The handle 20 also includes reflectors 226 secured thereto in either a permanent or removable fashion. The driving shaft 222 extends from the distal end 228 of the handle 220 to a driving head 230 sized and shaped to accommodate driving of bone screw. Extending parallel to the driving shaft 222 are sheathed anode and cathode electrodes 232, 234. The sheathed electrodes 232, 234, when extended, extend beyond the driving head 230 of the driving shaft 222. The sheathed anode and cathode electrodes 232, 234 are preferably retractable so as to not interfere with the surgeon during driving of a bone screw.

The sheathed electrodes 232, 234 are extended and retracted manually by the surgeon using an eyelet 236. Preferably, the eyelet is positioned in sufficient proximity to the handle 220 so that a surgeon can extend and retract the electrodes 232, 234 while holding the handle 220 and be able to depress the actuator 238 to apply the electrical stimulation. Accordingly, the handle includes a cavity (not shown) defined by appropriate stops to define the range of translation of the electrodes.

FIG. 11 is an elevation view of a surgical tap according to another aspect of the present disclosure. In this example, a surgical tap 240 is constructed for pedicle hole preparation, but is also capable of neurostimulation and providing navigational information. In this regard, the surgical tap 240 includes a handle 242 with a conductive shaft 244 extending therefrom. An insulating sheath 246 surrounds only a portion of the shaft so as to limit electrostimulation to the conductive tip 248. The conductive tip 248 includes a series of threads 250 that engage the pedicle or other bony structure during insertion of the tap. The threads 250 are formed such that a longitudinal recess or channel 252 is defined along the length of the tip.

Handle 242 has an actuator switch 254 that allows a user to selectively apply electrostimulation during insertion of the tip. As such, electrostimulation can be applied while the surgical tap is forming a pedicle screw pilot hole or probing of the pedicle. Energy is applied to the conductive tip 248 via conductor 256, which is connectable to an energy source of the neuromonitoring system, FIG. 1. Alternatively, batteries can be disposed in the handle and used to supply electrostimulating energy to the conductive tip 248.

The handle 242 also has three reflectors 258 which provide visual feedback to a camera (not shown) or other detection device to determine the position and orientation of the tap. One skilled in the art will recognize that other techniques may be used to track the position of the tap, such as electronic position sensors in the handle.

FIG. 12 shows a surgical probe 260 according to another embodiment of the present disclosure. Similar to the examples described above, probe 260 has a handle 262 with a series of reflectors 264 coupled to or otherwise formed thereon. Extending from the proximate end of the handle are jacks 266 for connecting the probe 260 to the energy source of the neuromonitoring system, FIG. 2. Extending from the distal end of the handle 262 is a conductive shaft 268 partially shrouded by an insulating sheath 270. The unsheathed portion of the shaft 268 is a conductive tip 272 capable of probing the pedicle or other bony structure. The handle also has an actuator 274 for selectively energizing the conductive tip 272 for the application of electrostimulation during probing.

FIG. 13 is a cross-sectional view of the conductive tip 272. As shown, the conductive shaft 268 includes an anode conductive portion 274 and a cathode conductive portion 276 separated from the anode conductive portion 274 by an insulator 278. This is further illustrated in FIG. 14. With this construction, electrostimulation is applied between the anode conduction portion 276 and the electrically isolated cathode conductive portion 274 for bipolar electrostimulation.

The illustrative tools described above are designed to not only perform a surgical function, but also apply electrostimulation to a neural structure of the patient. As described herein, with the aid image based navigation, a surgeon can move the instrument, visualize that movement in real-time, and apply electrostimulation (uni-polar and bi-polar) as desired at various instrument positions without the need for a separate stimulation instrument. Further, electrostimulation can also be applied to enhance navigation through the application of a leading electrostimulation pattern. In this regard, as the instrument is traversed through the patient anatomy, electrostimulation is automatically applied ahead of the tip of the instrument. As such, neurological information is automatically acquired as the instrument is moved and the visualization of patient anatomy automatically updated to incorporate the neurological information. Moreover, the neurological information can be used to localize, with better specificity, the actual location and orientation of neural structures. For example, electrostimulation with a broadcasting scope can be applied as the instrument is moved. If a neurological response is not measured, such a broad electrostimulation continues. However, if a neurological response is measured, a pinpointing electrostimulation can be repeatedly applied with decreasing coverage to localize the position of the stimulated neural structure.

Referring now to FIG. 15, in a further example, the leading electrostimulation can also be used to signal to the surgeon that the instrument is approaching a nerve or other neural structure. The signal may be a visual identifier on the GUI or in the form of an audible warning broadcast through the audio system described herein. In this regard, the integrated system determines the instantaneous position of the instrument at 280. The system then compares the position of the instrument with information regarding the anatomical makeup of the patient to determine the proximity of the instrument to neural structures that may not be readably visible on the anatomical visualization at 282. If the instrument is not near a neural structure 282, 284, the process loops back to step 280. If the instrument is at or near a previously identified neural structure 282, 286, the neural structure is identified or classified from an anatomical framework of the patient and/or the neurological response of the structure. Once the neural structure is identified 288, an appropriate signal is output 290 signaling that the instrument is near a neural structure. It is contemplated that the intensity and identification afforded the signal may be based on the type of neural structure identified as being proximal the instrument. For example, the volume and the pattern of an audible alarm may vary depending upon the type of neural structure. Further, in the example of audible proximity indicators, the volume and/or pattern of audible alarm may change as the instrument moves closer to or farther away from the neural structure. Thus, the audible signals provide real-time feedback to the surgeon regarding the position of the instrument relative to a neural structure. After the appropriate signal is output, the process returns to determining the position of the instrument at 280.

As described above, the integrated system is also capable of performing measurements between trajectories or instrument positions. Thus, for example, bone measurements can be done to determine if sufficient bone has been removed for a particular surgical procedure. For instance, the instrument can be tracked across the profile of a portion of a bone to be removed. The trajectory across the profile can then be stored as a trajectory. Following one or more bone removal procedures, the instrument can again be tracked across the bone now having a portion thereof removed. The system can then compute the differences between those trajectories and provide a quantitative value to the surgeon, via the GUI, for example, to assist the surgeon in determining if enough bone has been removed for the particular surgical procedure.

Also, the characteristics of the electrostimulation can be automatically adjusted based on the tracked instantaneous position of the instrument. That is, the integrated system, through real-time tracking of the instrument and a general understanding of patient anatomy layout from images, atlas models, and the like, can automatically set the intensity, scope, and type of electrostimulation based on the anatomy proximal the instrument when the surgeon directs application of electrostimulation. Rather than automatically set the electrostimulation characteristics, the system could similar display, on the GUI, the electrostimulation values derived by the system for consideration by the surgeon. In this regard, the surgeon could adopt, through appropriate inputs to the GUI, the suggested characteristics or define values different from those suggested by the system. Also, since an instrument could be used for bone milling or removal and electrostimulation, neurological responses could be measured during active milling or bone removal.

While an integrated surgical navigational and neuromonitoring system has been described, it is recognized that stand-alone systems may be communicatively linked to one another in a handshake fashion. Thus, through software modules, such as those described herein, the neuromonitoring information provided by a stand-alone neuromonitoring probe and system can be provided to a stand-alone surgical navigational system for the integrated visualization of navigational and neuromonitoring information.

As described herein, the integrated system is also capable of providing on-demand access to technical resources to a surgeon. Moreover, the integrated system is designed to provide a list of on-demand resources based on instrument position, neural structure position, or neural structure neuroresponse. As set forth in FIG. 16, the integrated system is designed to receive a user input 292 from the surgeon or other user requesting publication of a technical resource. Responsive to that input, the integrated system determines the instantaneous position of the instrument 294 when the request is made. Based on the instrument position, anatomical structures proximal the instrument are then determined 296. From the position of the instrument, the identified proximal anatomy, and, if applicable, the neurological response of a proximal neural structure, the system accesses corresponding portions of a technical resource database 298 to derive and display a list of related technical resources available for publication to the surgeon at 300. The list is preferably in the form of selectable computer data links displayed on the GUI for surgeon selection and may link to articles, publications, tutorials, maps, presentations, video, instructions, and manuals, for example. In response to a user selection on the GUI 302, the selected technical resource is uploaded from the database and published to the surgeon or other user at 304. It is contemplated that the integrated system may upload the technical resource from a local or remote database.

Another process capable of being carried out by the integrated system described herein is shown in FIG. 17. FIG. 17 sets forth the steps of a predictive process for providing feedback to a surgeon or other is assessing neural integrity. The process begins at step 306 with determining a position of the electrostimulation instrument when an electrostimulation is applied. The location of the stimulated neural structure is also determined at 308. Based on the location of the neural structure, the neural structure is identified 310. Identification of the neural structure can be determined from comparing anatomical information of the patient with previous neural maps, atlas models, anatomical maps, and the like. Based on identification of the neural structure, e.g., class, the neurological response of the neural structure to the electrostimulation is predicted 312. The predicted neurological response is then compared to the actual, measured neurological response at 314. The results of that comparison are then conveyed at 316 to the surgeon or other user with the GUI to assist with determining the neural integrity of the stimulated neural structure. Additionally, the visualization of the stimulated and measured neural structure can be automatically updated based on the comparison, e.g., color coded or annotated to indicate that the neurological response was not in line with that expected.

Figure 18:
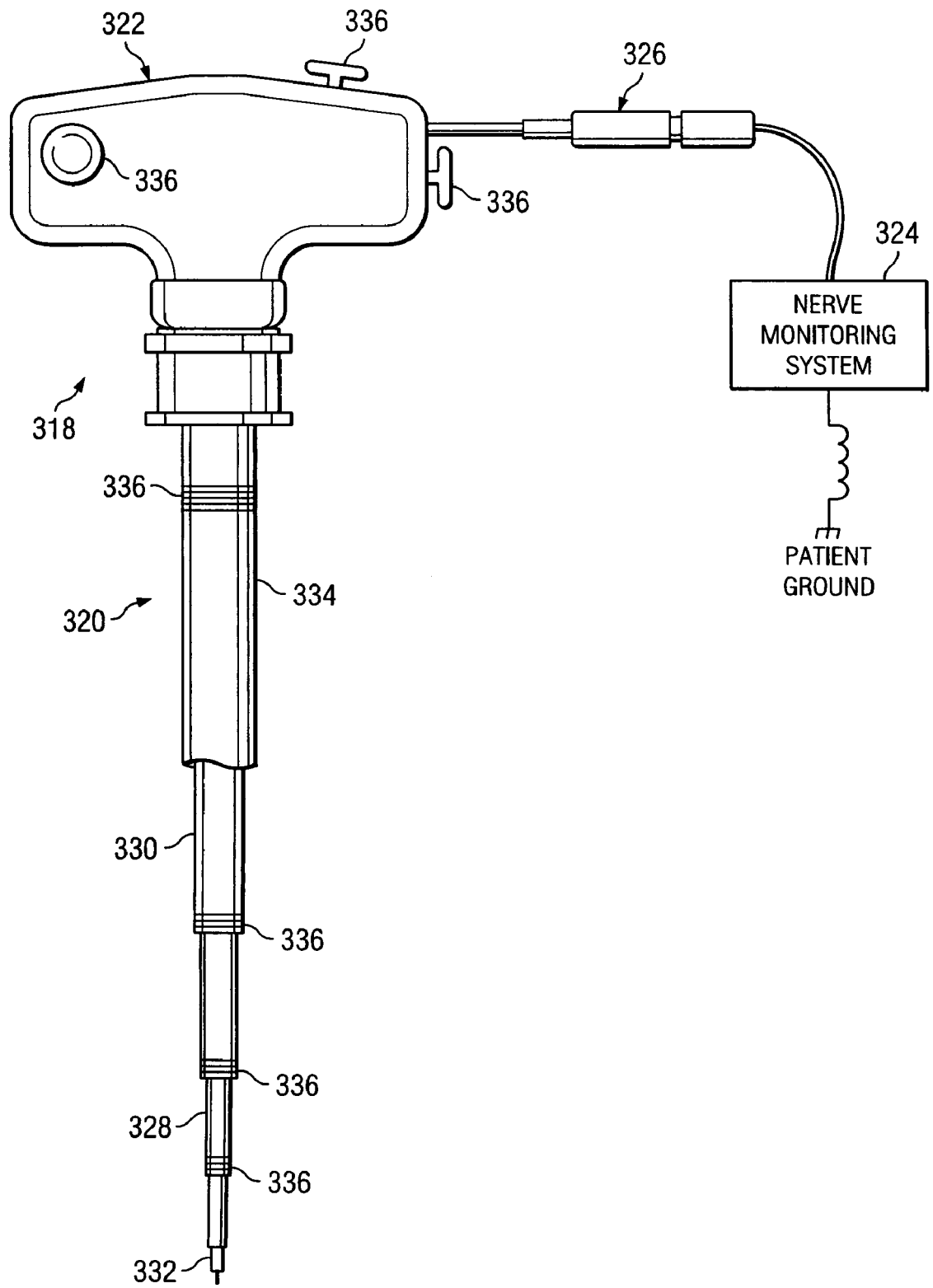
FIG. 18 is a neuromonitoring probe according to another aspect of the invention.

FIGS. 7-14 illustrate various examples of surgical instruments in accordance with the present disclosure. FIG. 18 illustrates another surgical instrument according to the present disclosure. Specifically, FIG. 18 illustrates a NIM probe 318 that can be used to apply electrostimulation to a neural structure. The NIM probe can also be used for forming a pilot hole in a pedicle such that neuromonitoring can be performed during pilot hole formation.

The illustrated NIM probe is similar in general construction to that described in U.S. Patent Application Publication No. 2006/0173521, the disclosure of which is incorporated herein by reference. The NIM probe 318 includes a needle assembly 320 and a handle assembly 322. Needle assembly 320 can be electrically connected to a nerve monitoring system 324 via lead 326. Lead 326 extends through handle assembly 322 and is electrically connected to stylet 328. The stylet 328 is positioned internally of an insulating cannula 330. In this regard, the stylet 328 distally projects from the cannula 330. The distally projecting portion of stylet 328 includes a tip portion 332 that can be used for piercing skin, soft or hard tissues, pedicle pilot hole formation, and applying an electrostimulus to a neural structure. The NIM probe 318 optionally includes a sheath 334 surrounding a portion of cannula 330 and/or stylet 328. Preferably, cannula 330 and sheath 334 are formed of non-electrically conductive material. In this regard, the unexposed portions of the stylet are electrically isolated from tissues adjacent the NIM probe when the tip portion 332 is energized.

The NIM probe also includes navigational sensors 336 positioned at various points on the cannula, sheath, and handle assembly 322. In one example, the sensors are passive devices, e.g., reflectors. In another example, the sensors are active devices, e.g., emitters or transmitters. In yet a further example, a combination of passive and active devices is used. The active devices may be powered by the energy supplied to the NIM probe from the nerve monitoring system 324. Alternatively, the active devices may be independently powered, such as with batteries. The sensors 336 communicate with a surgical navigation system, such as that described herein, that determines a position and/or orientation of the instrument in real-time. As described above, a user interface can then be updated to include a visualization of the instrument (or portions thereof, e.g., stylet tip) relative to patient anatomy to assist a surgeon with instrument navigation, and patient diagnosis.

While a probe, a retractor, a screwdriver, and a tap have been shown and described, it is contemplated that other surgical tools according to the present disclosure may be used to carry out surgical functions as well as apply electrostimulation, such as blunt dilators, awls, pedicle access needles, biopsy needles, drug delivery needles, ball tip probes, inner body dilators, spinal disc removal tools, inner body spacer tools, soft tissue retractors, gloves, finger covers, tool guides, and others. Additionally, it is contemplated that an implant, such as a pedicle screw, disc, or nucleus replacement, when coupled to a conductive portion of a surgical tool, may also be conductive and thus used to apply electrostimulation during implantation of the implant. For example, a bone screw may also be used to apply electrostimulation when engaged with the driving and conductive end of a driver. Also, while surgical instruments having reflectors for optically determining instrument position and orientation have been illustratively shown, the surgical instruments may include circuitry such as that described with respect to FIG. 6 for electromagnetically determining instrument position and orientation and inductively powering the electrostimulation and transmitter circuits. Furthermore, the surgical tools can be adapted to control parameters of the surgical navigational and neuromonitoring systems. It also contemplated that the surgical tools can communicate with the navigational and neuromonitoring systems via a wireless or wired connection. It is further contemplated that the magnitude of electrostimulation can be pre-defined or automatically determined based on the relative position and orientation of the instrument. Thus, the electrostimulation intensity and pattern can be automatically determined based on the position of the instrument.

The surgical instruments described herein illustrate various examples in which the present disclosure can be implemented. It is recognized that other instruments other than those described can be used. Further, preferably, the instruments are formed of bio-compatible materials, such as stainless steel. It is recognized however that other bio-compatible materials can be used. Also, it is recognized that non-tip portions of an instrument may be used for applying electrostimulation. For example, a dilator or retractor blade may be constructed such that multiple electrodes are defined along the length of the instrument. As such, electrostimulation could be selectively applied along the length of the instrument.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. Further, the embodiments of the present disclosure may be adapted to work singly or in combination over multiple spinal levels and vertebral motion segments. Also, though the embodiments have been described with respect to the spine and, more particularly, to vertebral motion segments, the present disclosure has similar application to other motion segments and parts of the body. In the claims, means-plus-function clauses are intended to cover the elements described herein as performing the recited function and not only structural equivalents, but also equivalent elements.

We claim:

1. A surgical tool capable of applying electrostimulation comprising:
    an instrument having a handle portion and a body member extending from the handle portion, the body member having an electrically conductive portion connected to an energy source and capable of applying electrostimulation energy provided by the energy source; and
    a tracking system associated with the instrument and operative to provide information regarding a position of the instrument on a display, the tracking system being configured to detect neurological information based on the electrostimulation energy applied by the instrument and provide the neurological information with the instrument position information on the display;
    wherein the electrically conductive portion has a distal end configured to removably couple to an electrically conductive implant and configured to apply electrostimulation energy through the electrically conductive implant into adjacent tissue.

2. The surgical tool of claim 1 wherein the handle portion includes an electrical lead connectable to the energy source, wherein the energy source is remote from the instrument.

3. The surgical tool of claim 1 wherein the energy source includes a battery pack disposed within the handle portion.

4. The surgical tool of claim 1 wherein the body member includes an electrically insulated outer surface area, and wherein the electrically conductive portion extends from the handle portion and internal to the insulated outer surface.

5. The surgical tool of claim 1 wherein the tracking system includes a set of reflectors connected to the instrument and operative to reflect energy that can be detected and analyzed by a navigation system to determine a real-time position of the instrument.

6. The surgical tool of claim 5 wherein the set of reflectors are connected to an outer surface of the handle portion.

7. The surgical tool of claim 1 wherein the tracking system includes a set of emitters connected to the instrument and operative to provide detectable energy that can be analyzed by a navigational system to determine a real-time position of the instrument.

8. The surgical tool of claim 7 wherein the set of emitters are powered by electrical energy provided to the instrument by the energy source.

9. The surgical tool of claim 1 wherein the instrument is capable of applying bi-polar electrostimulation.

10. The surgical tool of claim 1 wherein the instrument is a surgical probe.

11. The surgical tool of claim 1 wherein the instrument is a surgical tap.

12. The surgical tool of claim 1 wherein the instrument is a screwdriver.

13. The surgical tool of claim 1 wherein the instrument is a retractor.

14. The surgical tool of claim 1 wherein the instrument is capable of applying uni-polar electrostimulation.

15. The surgical tool of claim 1 wherein the electrically conductive implant includes a pedicle screw.

16. The surgical tool of claim 1 wherein the electrically conductive implant includes a nucleus replacement.

17. A surgical tool capable of applying electrostimulation comprising:
an instrument having a handle portion and a body member extending from the handle portion, the body member having an electrically conductive portion connected to an energy source and capable of applying electrostimulation energy provided by the energy source; and
a tracking system associated with the instrument and operative to provide information regarding a position of the instrument,
wherein the electrically conductive portion has a distal end configured to removably couple to an electrically conductive implant,
wherein the electrically conductive implant includes an artificial disc.

* * * * *